US 6,685,728 B2

(12) United States Patent
Sinnott et al.

(10) Patent No.: US 6,685,728 B2
(45) Date of Patent: Feb. 3, 2004

(54) THREADED SUTURE ANCHOR AND METHOD OF USE

(75) Inventors: M. Mary Sinnott, Logan, UT (US); Alan Chervitz, Palm Harbor, FL (US)

(73) Assignee: Stryker Endoscopy, San Jose, CA (US)

( * ) Notice: Subject to any disclaimer, the term of this patent is extended or adjusted under 35 U.S.C. 154(b) by 0 days.

(21) Appl. No.: 10/057,482

(22) Filed: Jan. 25, 2002

(65) Prior Publication Data
US 2003/0144696 A1 Jul. 31, 2003

(51) Int. Cl.[7] .............................................. A61B 17/04
(52) U.S. Cl. ...................................................... 606/232
(58) Field of Search ......................................... 606/232

(56) References Cited

U.S. PATENT DOCUMENTS

| 4,632,100 | A |   | 12/1986 | Somers et al. |  |
|---|---|---|---|---|---|
| 5,152,790 | A | * | 10/1992 | Rosenberg et al. | 623/13.14 |
| 5,370,662 | A |   | 12/1994 | Stone et al. |  |
| 5,411,523 | A | * | 5/1995 | Goble | 606/232 |
| 5,443,482 | A | * | 8/1995 | Stone et al. | 606/232 |
| 5,470,334 | A | * | 11/1995 | Ross et al. | 606/72 |
| 5,505,735 | A | * | 4/1996 | Li | 606/72 |
| 5,645,547 | A | * | 7/1997 | Coleman | 606/73 |
| 5,720,766 | A |   | 2/1998 | Zang et al. |  |
| 5,733,307 | A |   | 3/1998 | Dinsdale |  |
| 5,814,070 | A |   | 9/1998 | Borzone et al. |  |
| 5,824,011 | A |   | 10/1998 | Stone et al. |  |
| 5,904,704 | A | * | 5/1999 | Goble et al. | 606/232 |
| 5,964,783 | A |   | 10/1999 | Grafton et al. |  |
| 6,027,523 | A | * | 2/2000 | Schmieding | 606/232 |
| 6,045,573 | A | * | 4/2000 | Wenstrom et al. | 606/232 |
| 6,096,060 | A |   | 8/2000 | Fitts et al. |  |
| 6,117,162 | A |   | 9/2000 | Schmieding et al. |  |
| 6,214,031 | B1 |   | 4/2001 | Schmieding et al. |  |
| 6,290,702 | B1 |   | 9/2001 | Fucci et al. |  |
| 6,319,270 | B1 |   | 11/2001 | Grafton et al. |  |

* cited by examiner

Primary Examiner—Gary Jackson
(74) Attorney, Agent, or Firm—Workman Nydegger

(57) ABSTRACT

A suture anchor includes an elongated shaft having an exterior sidewall extending between a proximal end and an opposing distal end. A helical first thread is wound about and outwardly projects from the exterior sidewall of the shaft so as to extend between the proximal end and the distal end of the shaft. A first suture port transversely extends through at least a portion of the first thread at the proximal end of the shaft. The suture port is configured to receive a suture line.

53 Claims, 19 Drawing Sheets

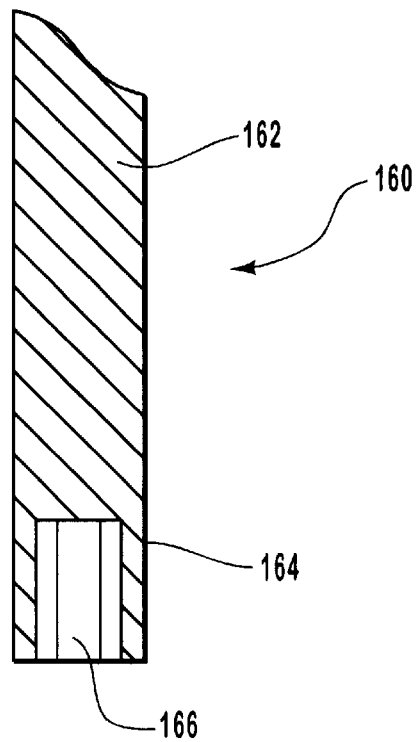
Fig. 20
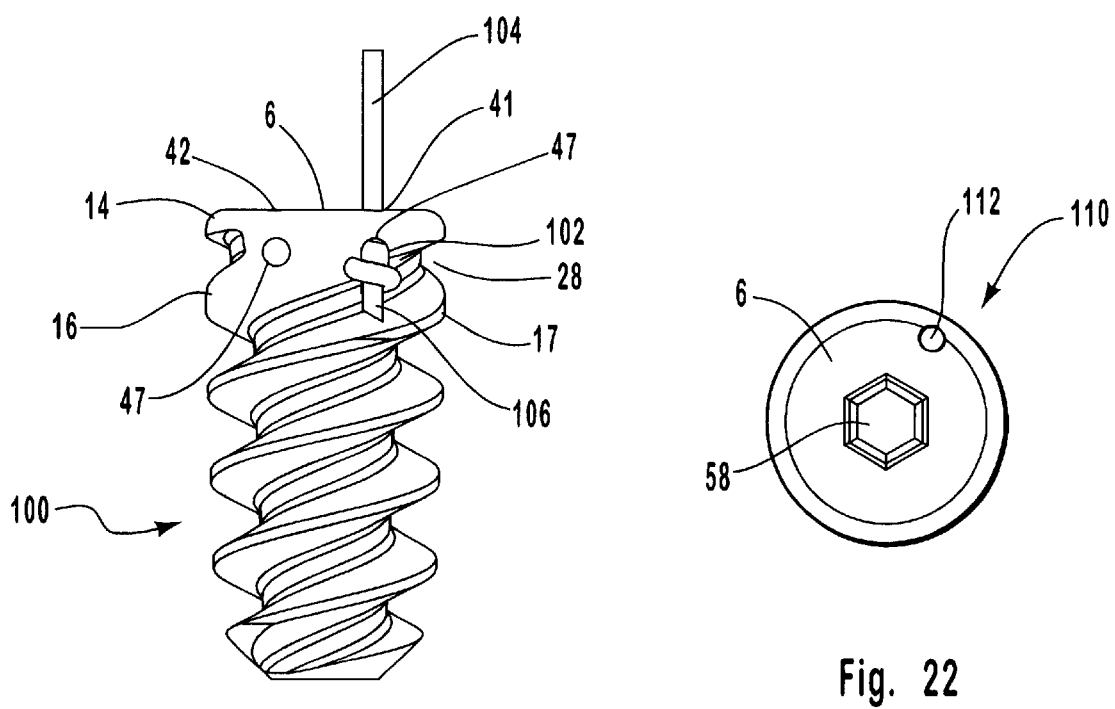
Fig. 21
Fig. 22

THREADED SUTURE ANCHOR AND METHOD OF USE

CROSS-REFERENCE TO RELATED APPLICATIONS

Not applicable.

BACKGROUND OF THE INVENTION

1. The Field of the Invention

The present invention relates to implantable suture anchors used for surgically attaching soft tissue to bone, as well as instrumentation and methods for deploying such anchors.

2. The Relevant Technology

One common type of orthopedic, i.e., bone related, injury is the tearing of soft tissue, such as tendons, ligaments, and muscles. Such injuries often result in at least a portion of the soft tissue being separated from the bone so that the soft tissue no longer functions in its intended manner. A common surgical procedure to remedy this injury is to mechanically secure the torn portion of the soft tissue back to the bone. Such mechanical attachment can be temporary in that the soft tissue eventually reattaches itself to the bone if held in contact therewith for a sufficient period of time.

A suture anchor is one type of mechanical device that is used to secure soft tissue to bone. Most suture anchors comprise a small metal or plastic fixture which has a suture line secured thereto. Conventional suture anchors come in a variety of different configurations. For example, some suture anchors are threaded so as to enable them to be screwed into the bone. Other suture anchors are designed to be wedged within a hole formed in the bone. In either event, once the suture anchor is secured to the bone, the suture line extending therefrom is used to tie or otherwise secure the soft tissue to the bone at the location of the implanted suture anchor.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 20 is a cross sectional side view of a driver for use in association with the suture anchor shown in FIG. 16;

FIG. 21 is a front side view of a suture anchor having alternative suture port configurations formed thereon;

FIG. 22 is a top plan view of an alternative embodiment of a suture anchor having a single suture port;

DETAILED DESCRIPTION OF THE PREFERRED EMBODIMENTS

Figure 1:
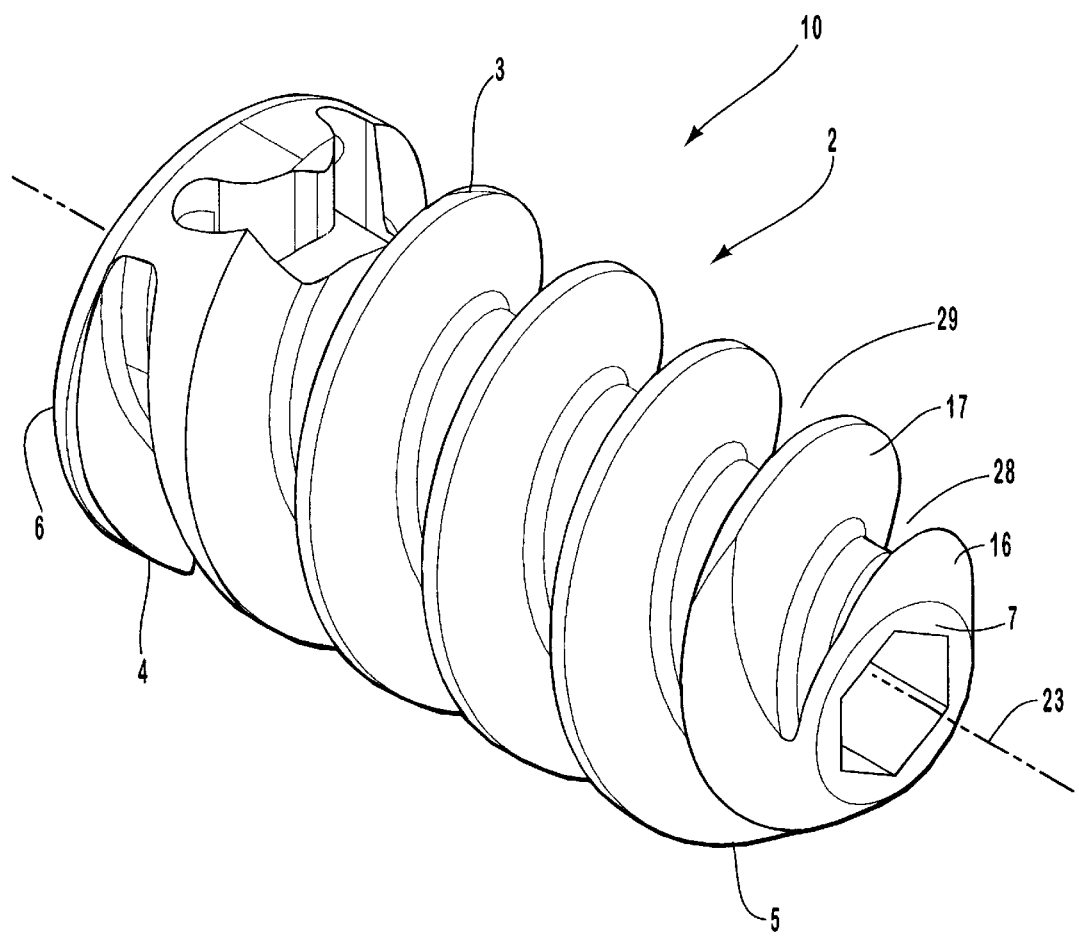
FIG. 1 is a perspective view of one embodiment of an inventive suture anchor.

Depicted in FIG. 1 is one embodiment of an inventive suture anchor 10 incorporating features of the present invention. Suture anchor 10 is configured for insertion into bone so as to subsequently facilitate attaching soft tissue, such as tendons, ligaments, muscles, or the like, either directly or indirectly to the bone. It will be appreciated, however, that suture anchor 10 may also be used in a variety of other applications.

Figure 2:
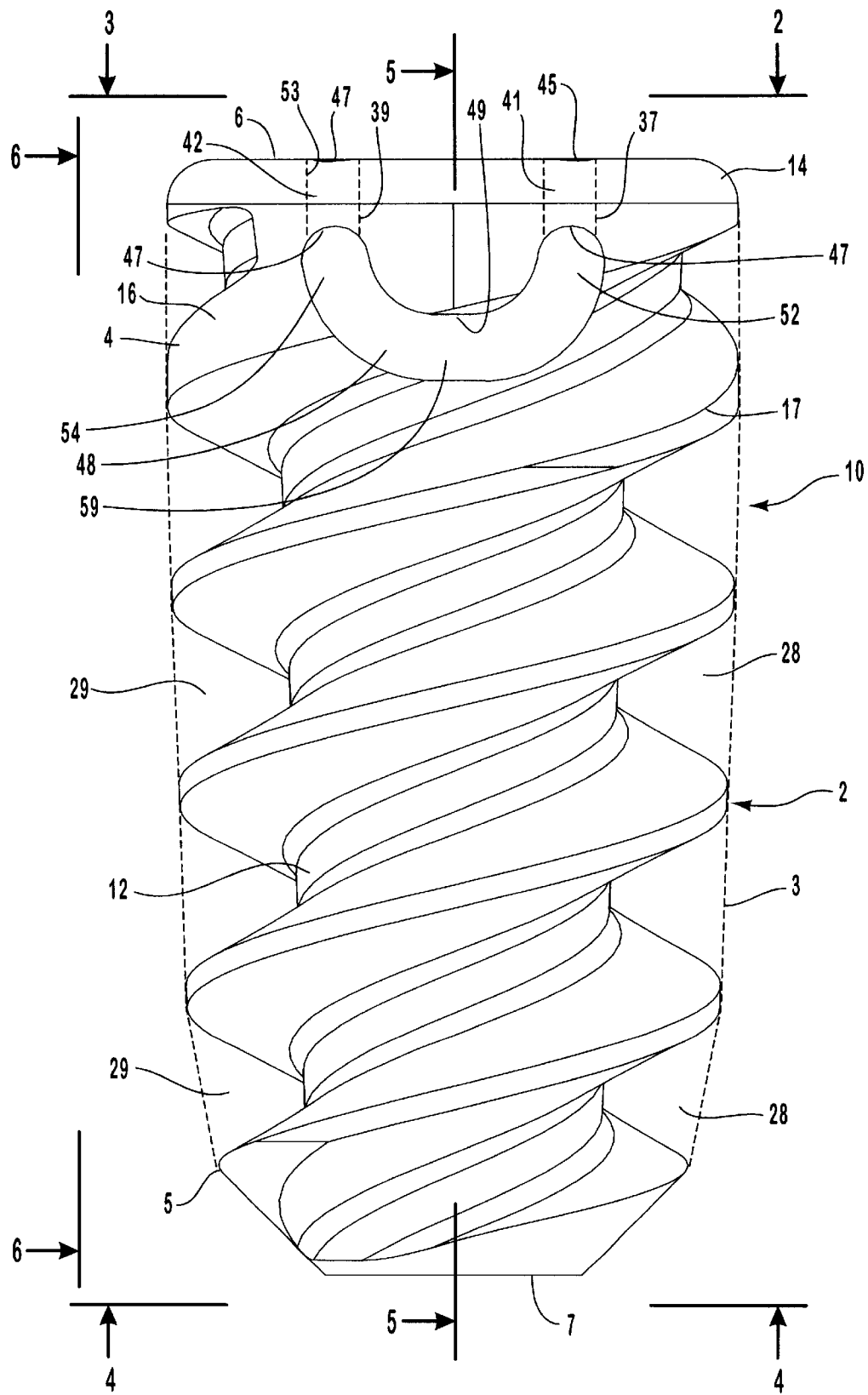
FIG. 2 is a front side view of the suture anchor shown in FIG. 1.

From a unitary perspective, suture anchor 10, as depicted in FIGS. 1 and 2, comprises a substantially cylindrical body 2 having an exterior sidewall (designated by dashed line 3 in FIG. 2) extending between a proximal end 4 and an opposing distal end 5. A central longitudinal axis 23 extends through body 2 between opposing ends 4 and 5. Proximal end 4 terminates at a proximal end face 6 (FIG. 3) while distal end 5 terminates at a distal end face 7 (FIG. 4). Exterior sidewall 3 tapers radially inward from proximal end 4 to distal end 5, the slope of the taper increasing at distal end 5.

Recessed into and about exterior sidewall 3 of body 2 so as to extend between proximal end 4 and distal end 5 of body 2 is a first helical groove 28. A second helical groove 29, intertwined with first helical groove 28, is also recessed into and about exterior sidewall 3 of body 2 so as to extend between proximal end 4 and distal end 5 of body 2. Each helical groove 28 and 29 terminates distal of proximal end face 6.

Figure 5:
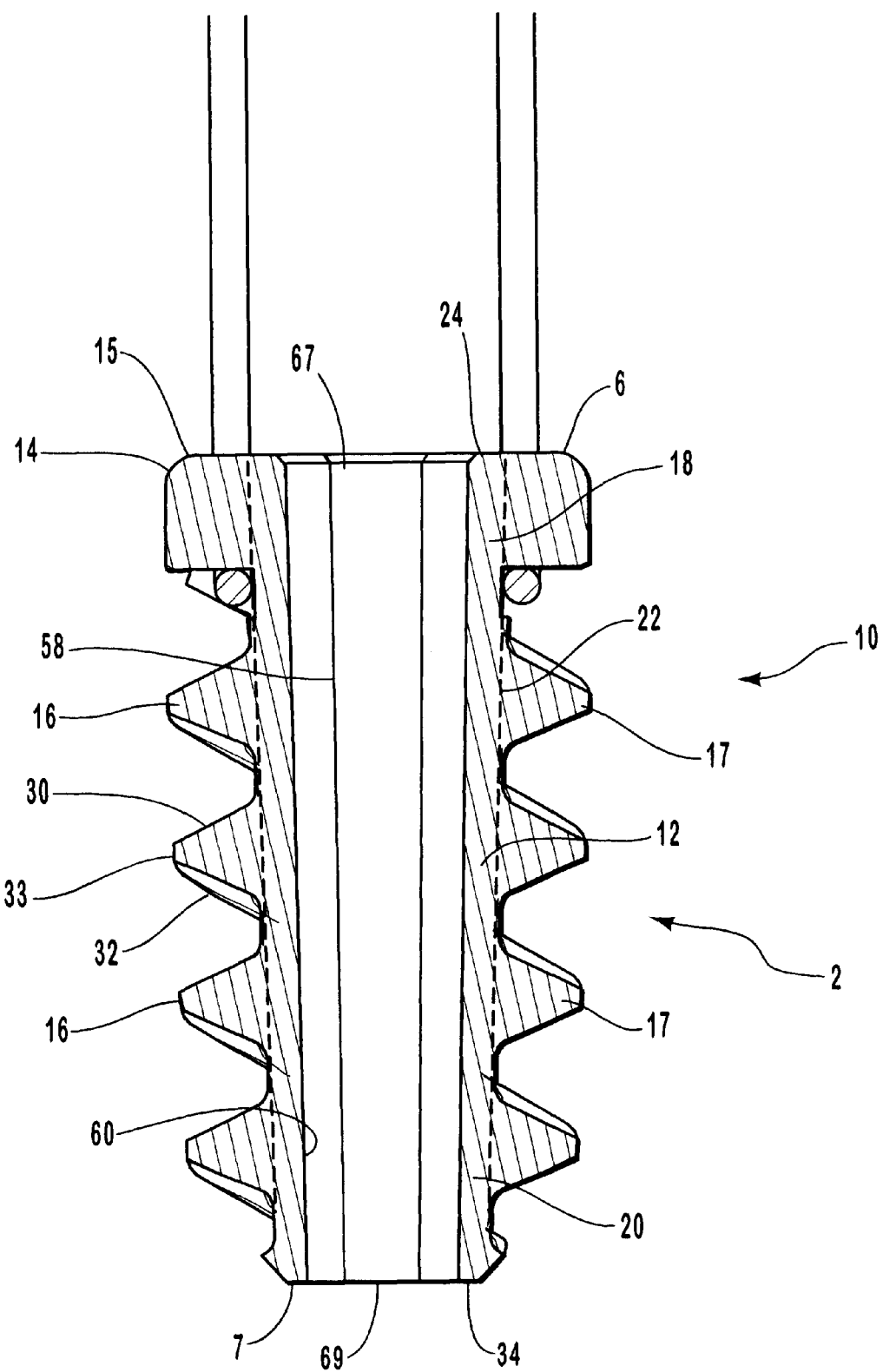
FIG. 5 is a cross sectional side view of the suture anchor shown in FIG. 1.

In contrast to describing suture anchor 10 from a unitary perspective, suture anchor 10 can also be described in terms of its structural elements. For example, in general suture anchor 10 comprises an elongated shaft, an annular flange disposed at one end of the elongated shaft, and first and second helical threads wound around and outwardly projecting from the elongated shaft. More specifically, as depicted in FIG. 5, a tubular elongated shaft 12 is shown having an exterior sidewall (designated by dashed line 22 in FIG. 5) extending between a proximal end 18 and an opposing distal end 20. Proximal end 18 terminates at a proximal end face 24 which forms a portion of proximal end face 6 of body 2. Distal end 20 of shaft 12 terminates at a distal end face 34 which can comprise part or all of distal end face 7 of body 2. As will be discussed below in greater detail, shaft 12 also has an interior surface 60 bounding a bore 58 extending between proximal end 18 and distal end 20 of shaft 12.

Shaft 12 is substantially cylindrical in shape, thus having a substantially circular transverse cross-section. In the embodiment depicted, exterior sidewall 22 of shaft 12 slopes radially inward from proximal end 18 toward distal end 20 so as to have a substantially frustoconical configuration. Alternatively, shaft 12 can be a pure cylinder having a constant diameter along its length. It is also appreciated that shaft 12 can be formed in a variety of other shapes without departing from the scope of the present invention. In one embodiment, shaft 12 has a maximum outer diameter in a range from about 2.5 mm to about 4 mm and a length in a range between about 10 mm to about 25 mm. Depending on the intended use, however, other dimensions can also be used.

Figure 6:
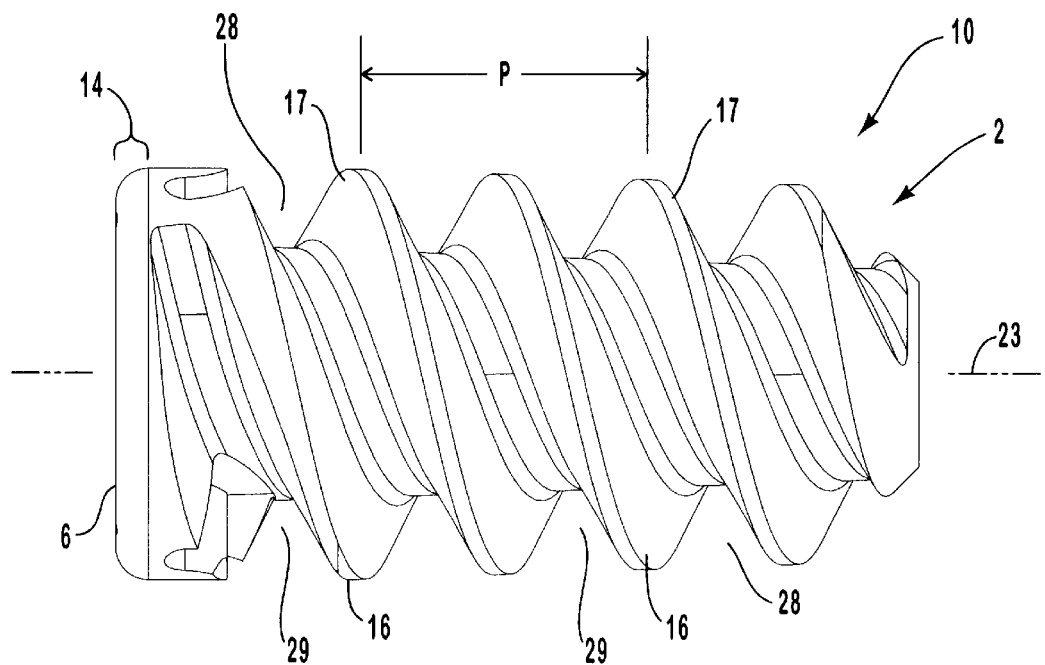
FIG. 6 is a right side view of the suture anchor shown in FIG. 1.

As depicted in FIGS. 5 and 6, a flange 14 radially outwardly projects from proximal end 18 of shaft 12 so as to encircle shaft 12. More specifically, as mentioned above, first and second helical grooves 28 and 29 terminate prior to reaching proximal end face 6 of body 2. Flange 14 comprises that portion of body 2 that extends between the proximal terminus of helical grooves 28 and 29 and proximal end face 6. Flange 14 has a proximal end face 15. Proximal end face 15 of flange 14 and proximal end face 24 of shaft 12 combine to form proximal end face 6 of body 2. In alternative embodiments, flange 14 need not completely encircle shaft 12. For example, flange 14 can comprise two or more discrete portions that outwardly project from proximal end 18 of shaft 12. Furthermore, flange 14 can be configured in a variety of polygonal or irregular configurations.

Flange 14 can be integrally formed with shaft 12, for example, by injection molding. Alternatively, flange 14 can be discretely formed, such as in the form of a disc or collar, and then separately secured to shaft 12 such as by friction fit, adhesions, or other forms of mechanical attachment. Flange 14 typically has a maximum outer diameter in a range between about 5 mm to about 8 mm and a thickness in a range between about 1 mm to about 3 mm. Depending on the intended use, however, other dimensions can also be used.

Depicted in FIGS. 2 and 5, a first helical thread 16 intertwined with a second helical thread 17 each wind about and outwardly project from exterior sidewall 22 of shaft 12 so as to extend in a helical path between flange 14 and distal end 20 of elongated shaft 12. Helical grooves 28 and 29, as previously discussed, are bound between helical threads 16 and 17. Each helical thread 16 and 17 has a proximal face 30 directed toward proximal end 18 of elongated shaft 12 and an opposing distal face 32 directed toward distal end 20 of elongated shaft 12. Opposing faces 30 and 32 each slope to an intersecting outside edge 33. As such, each thread 16, 17 has a substantially V-shaped transverse cross section that facilitates cutting into bone as suture anchor 10 is threaded into bone. Outside edges 33 form a portion of exterior sidewall 3 of body 2 as previously discussed.

The maximum outer diameter of threads 16 and 17 decreases toward distal end 20 of shaft 12. Furthermore, the height of threads 16 and 17, i.e., the distance extending between exterior sidewall 22 of shaft 12 and outside edge 33 of helical threads 16, 17, decreases at distal end 20 of shaft 12. As a result of this inward tapering, helical threads 16 and 17 are configured for self-tapping into bone once initial threading into the bone is started. In alternative embodiments, it is appreciated that various combinations of adjusting the tapered slope of exterior sidewall 22 of shaft 12 and adjusting the height of helical threads 16 and 17 along the length of shaft 12 can be used to control the change in the maximum outer diameter of helical threads 16 and 17 along the length of shaft 12.

Furthermore, in an alternative to forming threads which are self-tapping, it is also appreciated that threads 16 and 17 can be conventional threads that are configured for threading into a pre-tapped hole formed in the bone.

In one embodiment, threads 16 and 17 are configured to facilitate quick and easy insertion into bone while maximizing the ability to retain suture anchor 10 within the bone, i.e., prevent suture anchor 10 from being unintentionally pulled out of the bone. Features of helical threads 16 and 17 that relate to these properties include the height of the helical threads, as defined above, and the pitch of the helical threads. In general, the greater the height of helical threads 16, 17 the more bone matter that is caught between helical threads 16, 17, thereby better securing suture anchor 10 within the bone. As the thread height increases, however, more bone material must be displaced by helical threads 16, 17, thereby making it more difficult to rotate suture anchor 10. Furthermore, larger helical threads can be potentially weaker. In one embodiment helical threads 16 and 17 have a maximum height in a range between about 0.75 mm to about 1.5 mm. Depending on the intended use, however, other dimensions can also be used.

The pitch P, as depicted in FIG. 6, is the distance from any point on a select helical thread 16, 17 to a corresponding point on an adjacent helical winding of the same thread measured parallel to central longitudinal axis 23. Accordingly, by increasing the pitch of a thread, the helical slope of the thread increases and the number of helical windings of the thread per given length decreases. In one embodiment of the present invention, it is desirable to increase the pitch of helical threads 16, 17 since by so doing, fewer turns are required to completely screw suture anchor 10 into the bone. As a result, suture anchor 10 is more easily and quickly inserted.

By increasing the thread pitch, however, there is less thread length engaging with the bone to prevent unwanted pull-out of suture anchor 10. Accordingly, in the present embodiment two intertwining threads are used as opposed to a singe thread. This configuration enables the use of a relatively large thread pitch to facilitate quick insertion while providing a significant portion of thread length to directly engage with the bone, thereby preventing unwanted pull-out of suture anchor 10 from the bone. In one embodiment where dual threads are used, each thread has a maximum pitch P in a range between about 4 mm to about 5 mm. Depending on the intended use, however, other dimensions can also be used.

In an alternative embodiment, it is appreciated that the dual helical threads 16, 17 can be replaced with a single helical thread or three or more intertwining helical threads. Where a singe thread is used, the pitch is typically in a range between about 2.25 mm to about 2.75 mm.

Figure 3:
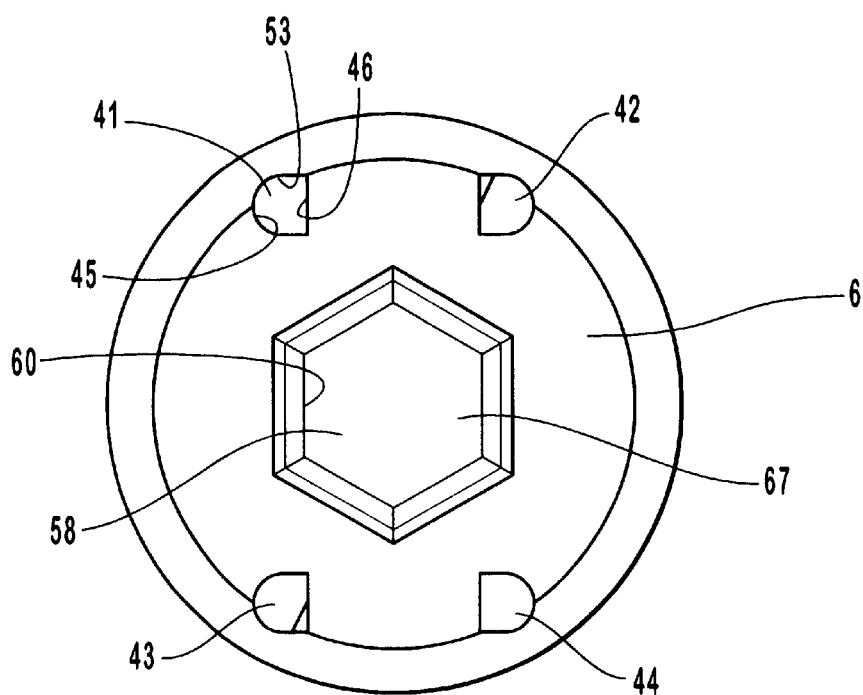
FIG. 3 is a top plan view of the suture anchor shown in FIG. 1.
Figure 4:
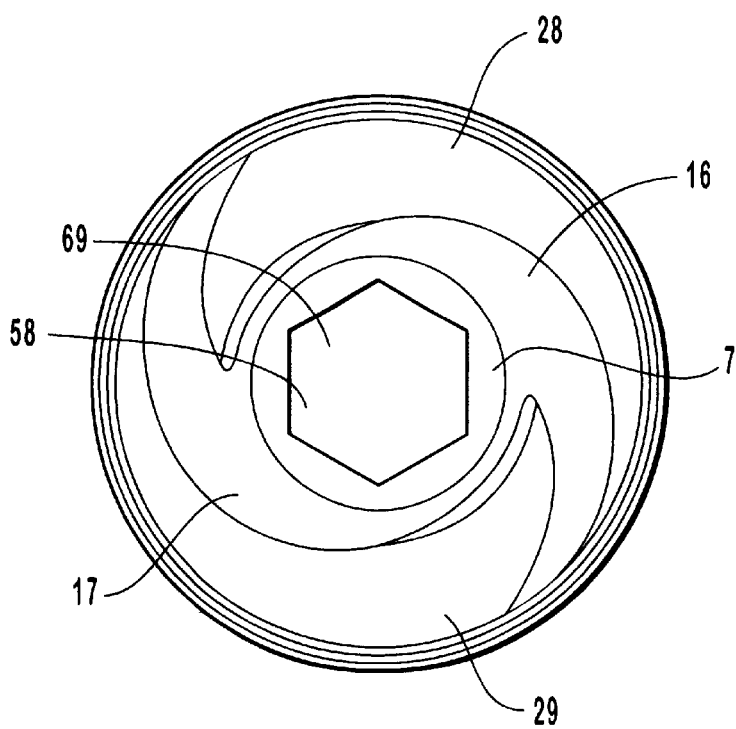
FIG. 4 is a bottom plan view of the suture anchor shown in FIG. 1.

Depicted in FIG. 3, four spaced apart suture ports 41–44 project into proximal end face 6 of body 2 in substantially parallel alignment with central longitudinal axis 23. As used in the specification and appended claims, the term "suture port" is intended to mean a hole or passageway through which a suture line can be inserted, the hole or passageway being completely encircled by one or more bounding structures such that the suture line can only be removed from the hole or passageway by passing an end of the suture line through the hole or passageway. Accordingly, an open slot or recessed channel does not constitute a "suture port." The term "suture line" as used in the specification and appended claims is intended to mean conventional surgical suture or any other type of line, cord, thread, or the like.

As shown in FIG. 2, each suture port 41 and 42 is bounded by an interior surface 53 extending between a proximal end 45 and an opposing distal end 47. Proximal end 45 of each suture port 41, 42 is flush with proximal end face 6 of body 2. Although interior surface 53 can be circular, polygonal or any other desired configuration, in the embodiment depicted in FIG. 3, interior surface 53 has a rounded U-shaped portion 45 and a flat portion 46. Flat portions 46 of suture ports 41 and 42 are positioned to oppositely face each other.

Interior surface 53 bounding each suture port 41 and 42 is comprised of annular flange 14 and/or shaft 12. Furthermore, in the embodiment depicted in FIG. 2, each suture port 41 and 42 passes though a corresponding portion 37 and 39, respectively, of first thread 16. Although not required, suture ports 41 and 42 are positioned such that a plane extending between suture ports 41 and 42 in parallel alignment with longitudinal axis 23 does not intersect with bore 58.

Figure 7:
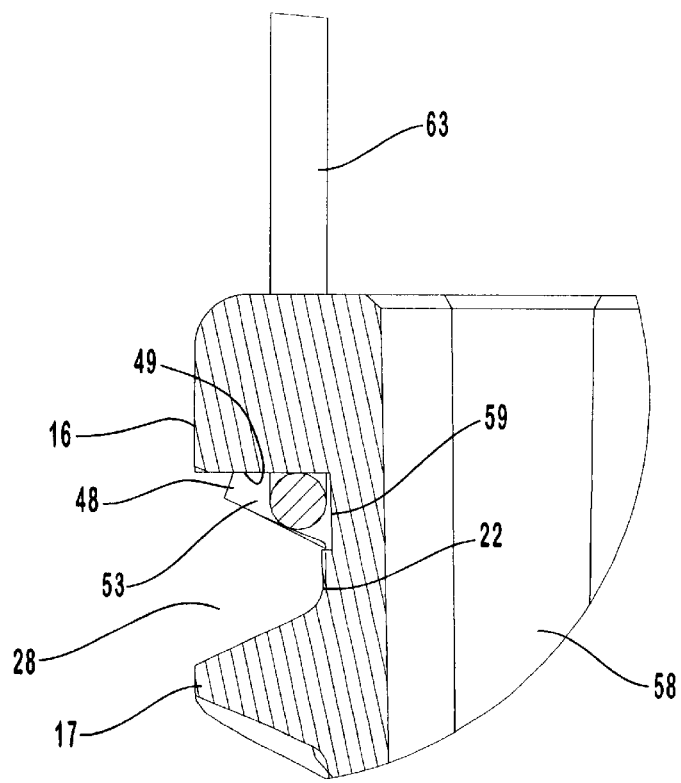
FIG. 7 is an enlarged cross sectional side view of the proximal end of the suture anchor shown in FIG. 5.

An open substantially U-shaped channel 48 is recessed within first thread 16 at proximal end 4 of body 2. Channel 48 has a substantially U-shaped upper side wall 49 extending between a first end 52 and an opposing second end 54. First end 52 communicates with distal end 47 of suture port 41 while second end 54 communicates with distal end 47 of suture port 42. A central portion 53 of channel 48 is formed between opposing ends 52 and 54. As depicted in FIGS. 2 and 7, central portion 53 intersects with helical groove 28 so as to openly communicate therewith. Furthermore, although not required, central portion 53 of channel 48 has an inside face 59 that is recessed within exterior sidewall of 22 of shaft 12.

Figure 8:
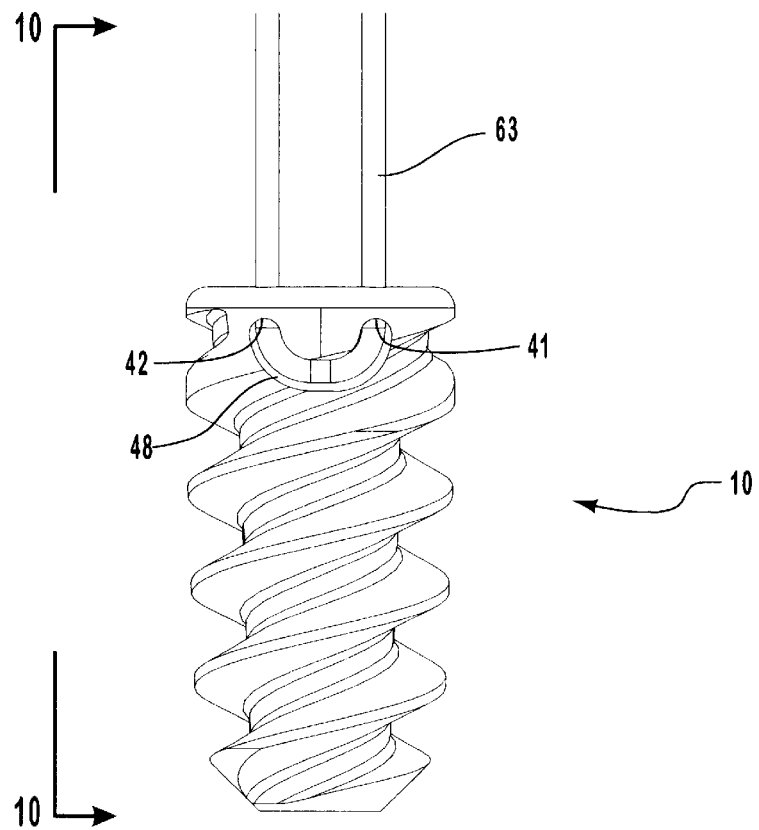
FIG. 8 is a front side view of the suture anchor shown in FIG. 2 having a suture line attached thereto.

As depicted in FIGS. 7 and 8, channel 48 operates with suture ports 41 and 42 such that a suture line 63 can be inserted through one of suture ports 41 and 42, feed along channel 48, and then passed out through the other of suture ports 41 and 42. As a result, suture line 63 is slidably connected to suture anchor 10 in a substantially U-shaped configuration. In the embodiment depicted, channel 48 is open to facilitate ease in manufacture and to enable easy threading of suture line 63 into and out of suture ports 41 and 42. In an alternative embodiment channel 48 can be completely enclosed such that channel 48 and suture ports 41 and 42 form a single continuous U-shaped suture port.

As will be discussed below in greater detail, as helical threads 16 and 17 of suture anchor 10 are screwed into bone, the bone fills helical grooves 28 and 29. Channel 48 is recessed within first thread 16 such that suture line 63 is protected within channel 48 from unintentional trauma produced by the bone as suture anchor 10 is screwed into the bone. More specifically, as suture anchor 10 is screwed into the bone, suture line 63 can be completely disposed within channel 48 such that the bone merely covers helical thread 16 and channel 48 without contacting suture line 63. Alternatively, a portion of suture line 63 may project from channel 48 into helical groove 28. Channel 48 is sufficiently large, however, that as the bone fills helical groove 28, the bone merely pushes suture line 63 into first channel 48 without damaging suture line 63.

In one embodiment suture line 63 is free to slide within channel 48 and suture ports 41 and 42 after suture anchor 10 is screwed into bone. Alternatively, the bone may sufficiently bias against suture line 63 to preclude or limit movement of suture line 63 once suture anchor 10 is screwed into the bone.

In contrast to extending parallel to longitudinal axis 23, suture ports 41 and 42 can be curved or extend at an angle relative to longitudinal axis 23. Furthermore, depending on the dimensions and configuration of shaft 12, flange 14, and threads 16, 17; open channel 48 can be formed so that one or more of suture ports 41 and 42 is positioned or oriented to extend exclusively through shaft 12, flange 14, or helical thread 16 or can extend through or partially through combinations of shaft 12, flange 14, and/or helical thread 16.

Figure 9:
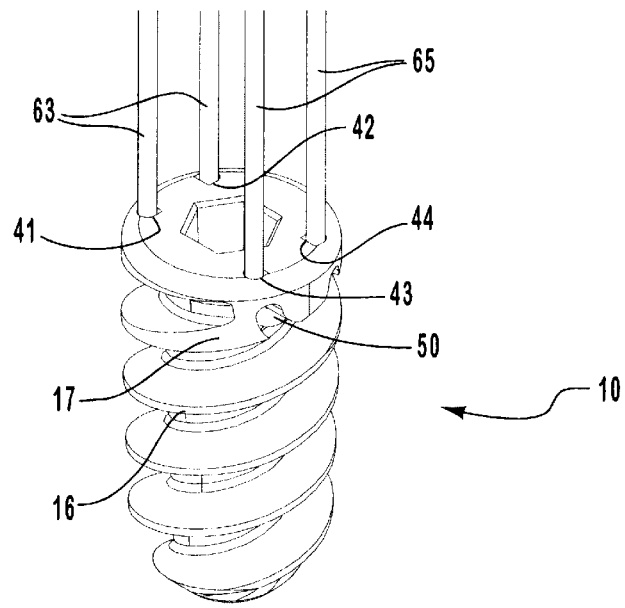
FIG. 9 is a perspective view of the suture anchor shown in FIG. 1 having two suture lines attached thereto.
Figure 10:
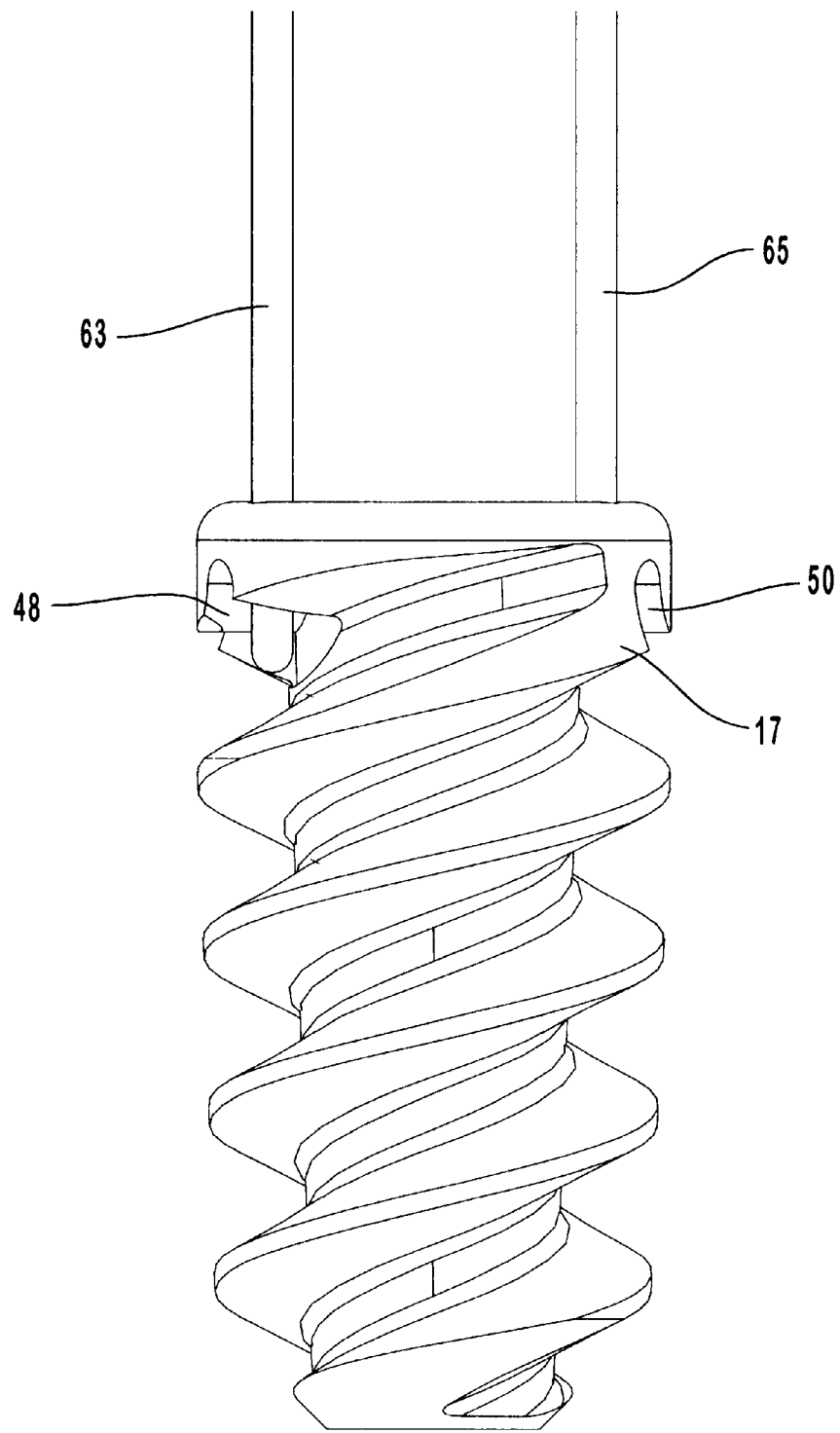
FIG. 10 is a right side view of the suture anchor shown in FIG. 2.

As depicted in FIGS. 9 and 10, suture ports 43 and 44 are formed on a side of suture anchor 10 opposite of suture ports 41, 42 and extend through portions of second helical thread 17. Suture ports 43 and 44 have the same positioning, configuration and alternative designs as discussed above with regard to suture ports 41 and 42. Also recessed within second helical thread 17 is an open channel 50 having the same configuration as channel 48, like elements being identified by like reference characters. Channel 50 facilitates communication between suture ports 43 and 44 and enables a suture line 65 to be disposed therein. Channel 50 and suture ports 43 and 44 operate with suture line 65 in the same manner as discussed above with regard to channel 48 and suture ports 41 and 42. Likewise, alternatives as discussed with channel 48 and suture ports 41 and 42 are also applicable to channel 50 and suture ports 43 and 44.

In one embodiment of the present invention, means are also provided for mechanically engaging at least a portion of shaft 12 so as to enable rotational placement of shaft 12 (hereinafter, "engaging means"). By way of example and not by limitation, as depicted in FIG. 5 one example of the engaging means comprises bore 58. Bore 58 is disposed along central longitudinal axis 23 so as to extend entirely through elongated shaft 12. More specifically, bore 58 is bounded by interior surface 60 of shaft 12 that extends between proximal end 18 and distal end 20 of shaft 12. Bore 58 has a proximal opening 67 formed on proximal end face 24 of shaft 12 and a distal opening 69 formed on distal end face 34 of shaft 12.

In one embodiment interior surface 60 of shaft 12 slopes radially inward toward distal end 20. In an alternative embodiment interior surface 60 can be cylindrical having a constant inside diameter extending between opposing ends. As perhaps best seen in FIG. 3, bore 58 has a hexagonal transverse cross section. In alternative embodiments, the transverse cross section of bore 58 can be any configuration such that when an driver, as discussed below, is complementary received within bore 58, rotation of the driver facilitates rotation of shaft 12. By way of example and not by limitation, the transverse cross section can be an ellipse, any polygonal configuration, or any other irregular configuration shape that is not a perfect circle. Furthermore, in the embodiment depicted bore 58 has a polygonal configuration that extends along the entire length of shaft 12. This configuration uniformly distributes the force produced by the driver along the entire length shaft 12. In an alternative embodiment, however, only a portion of bore 58 needs to directly engage the driver in complementary mating. As such, the shape of interior surface 60 of shaft 12 can change along the length thereof.

Figure 11:
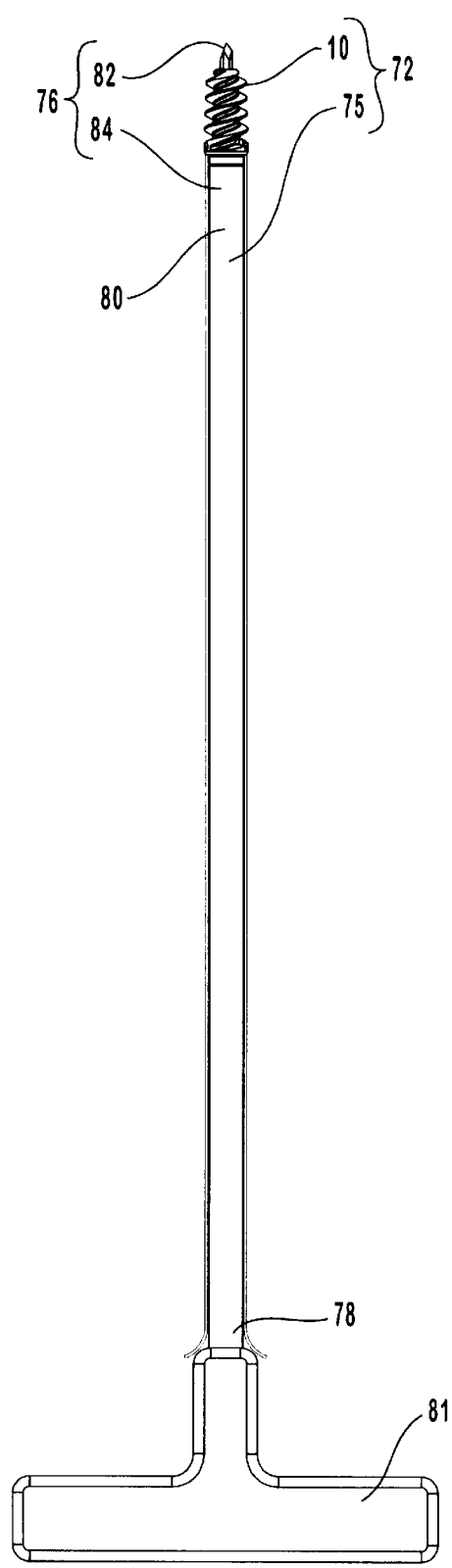
FIG. 11 is a right side view of a suture assembly including a driver having the suture anchor shown in FIG. 1 attached thereto.
Figure 12:
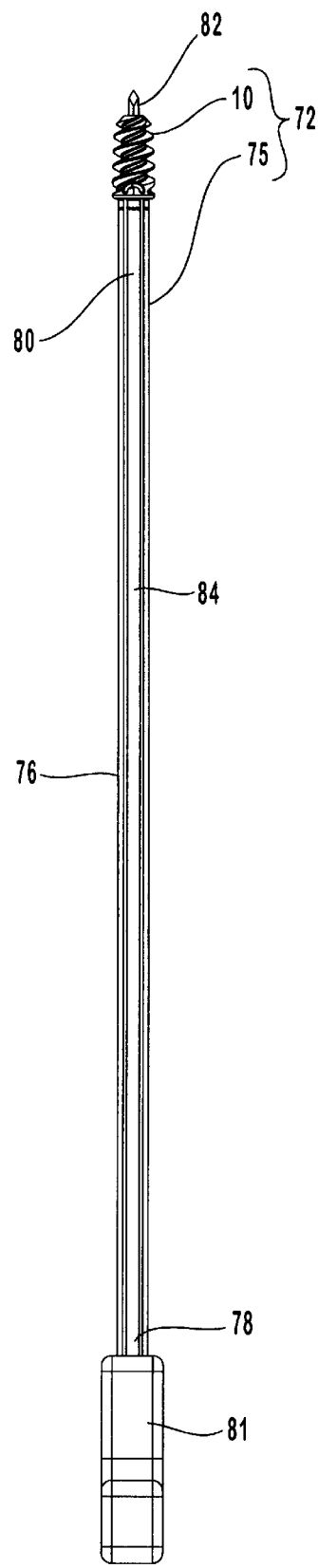
FIG. 12 is a front side view of the suture anchor assembly shown in FIG. 11.

Depicted in FIGS. 11 and 12 is one embodiment of a suture anchor assembly 72. Suture anchor assembly 72 comprises a driver 75 having suture anchor 10 mounted thereon. Driver 75 comprises a drive rod 76 having a proximal end 78 and an opposing distal end 80. Positioned at proximal end 78 of drive rod 76 is a handle 81. Drive rod 76 comprises a drive portion 82 and a body portion 84 extending between drive portion 82 and handle 81

Figure 13:
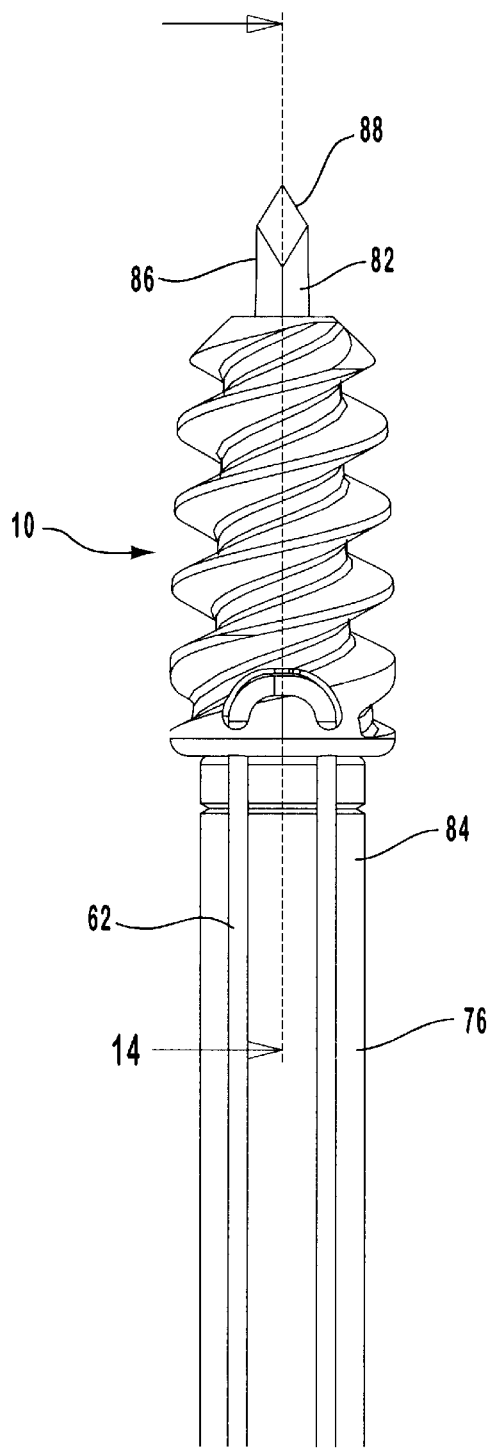
FIG. 13 is an enlarged side view of the distal end of the suture anchor assembly shown in FIG. 12.
Figure 14:
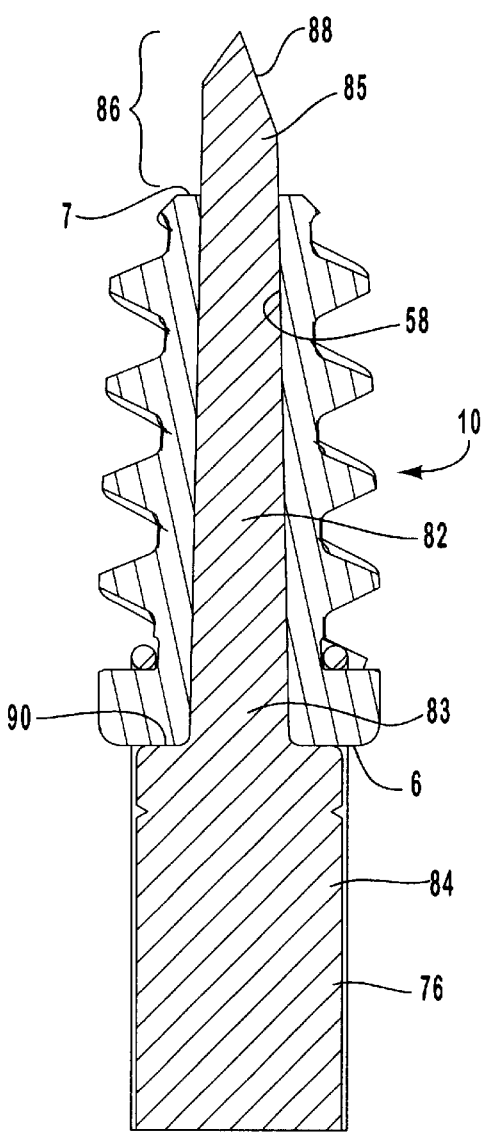
FIG. 14 is a cross sectional side view of the suture anchor assembly shown in FIG. 13.

Depicted in FIGS. 13 and 14, drive portion 82 has a proximal end 83 and an opposing distal end 85. Proximal end 83 of drive portion 82 intersects with body portion 84 at an annular outwardly projecting shoulder 90. Positioned at distal end 85 of drive portion 82 is a tip 86 having a plurality of sharpened edges 88.

During assembly, drive portion 82 of drive rod 76 is received within bore 58 such that proximal end face 6 of suture anchor 10 is biased against shoulder 90 of driver 75. In this position, tip 86 having sharpened edges 88 projects past distal end face 7 of suture anchor 10. As discussed above, drive portion 82 of drive rod 76 has a transverse cross section that is complementary to the transverse cross-section of bore 58 such that drive portion 82 complementary mates with bore 58 when received therein. As a result of the complementary mating between drive portion 82 and bore 58, rotation of drive rod 76 facilitates rotation of elongated shaft 12 and thus rotation of suture anchor 10.

Figure 15:
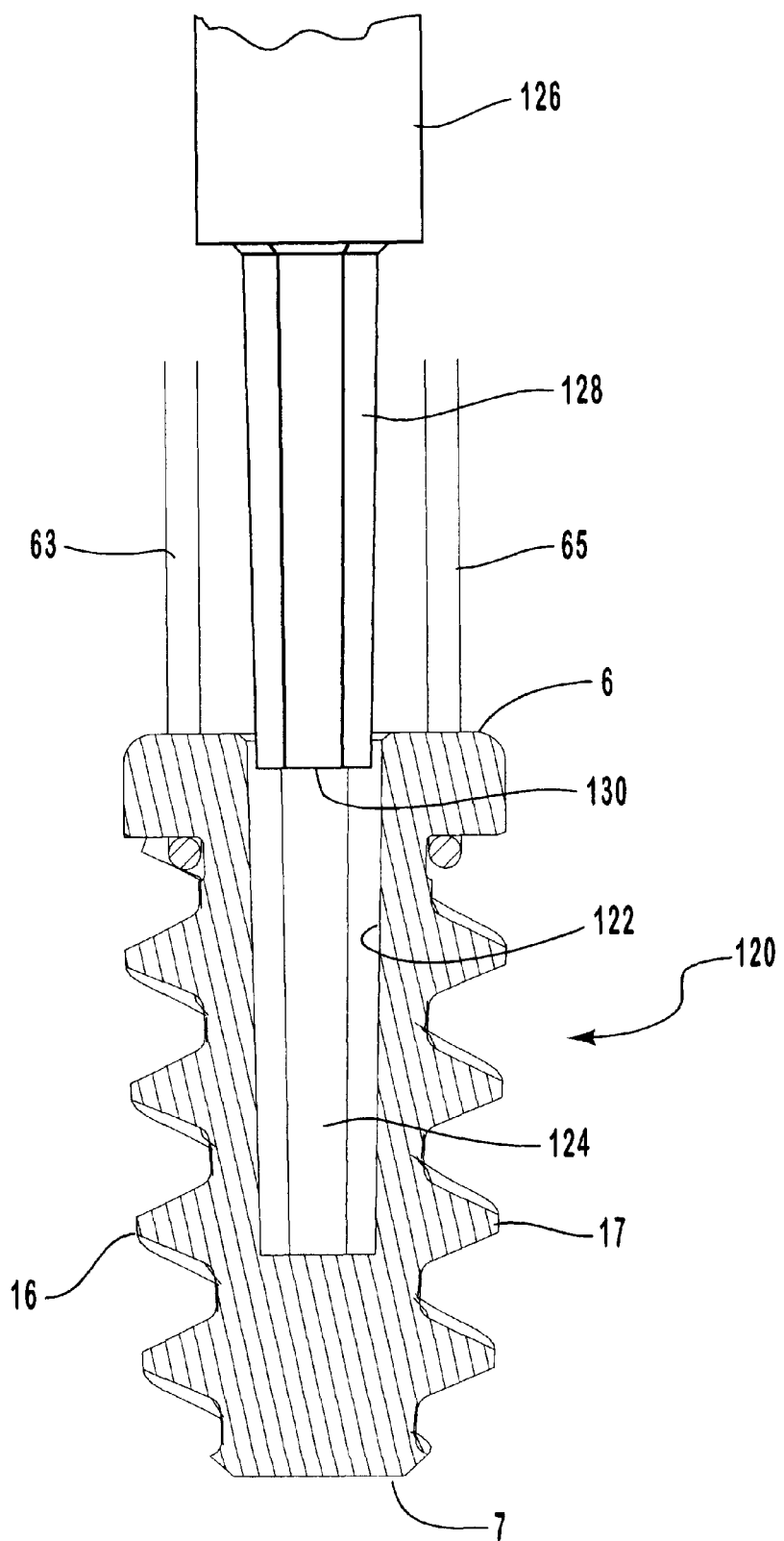
FIG. 15 is a cross sectional side view of an alternative embodiment of a suture anchor having a socket formed therein.

Depicted in FIG. 15 is another alternative embodiment of a suture anchor 120 wherein like elements between suture anchor 10 and 120 are identified by like reference characters. In contrast to bore 58 which extends all the way through suture anchor 10, suture anchor 120 has an interior surface 122 that bounds a bore which extends from proximal end face 6 distance toward distal end face 7. As such, interior surface 122 bound a closed end socket 124. A drive rod 126 includes a drive portion 128 that terminates at a blunt end 130. Drive portion 128 is configured to be received within socket 124 such that rotation of drive rod 126 facilitates rotation of suture anchor 120. As such, at least a portion of drive portion 128 and socket 124 have complementary transverse cross sections that are non-circular. For example, a portion of drive portion 128 and/or socket 124 can be polygonal while the remainder is circular. Socket 124 is another alternative embodiment of the engagement means as previously discussed.

Figure 16:
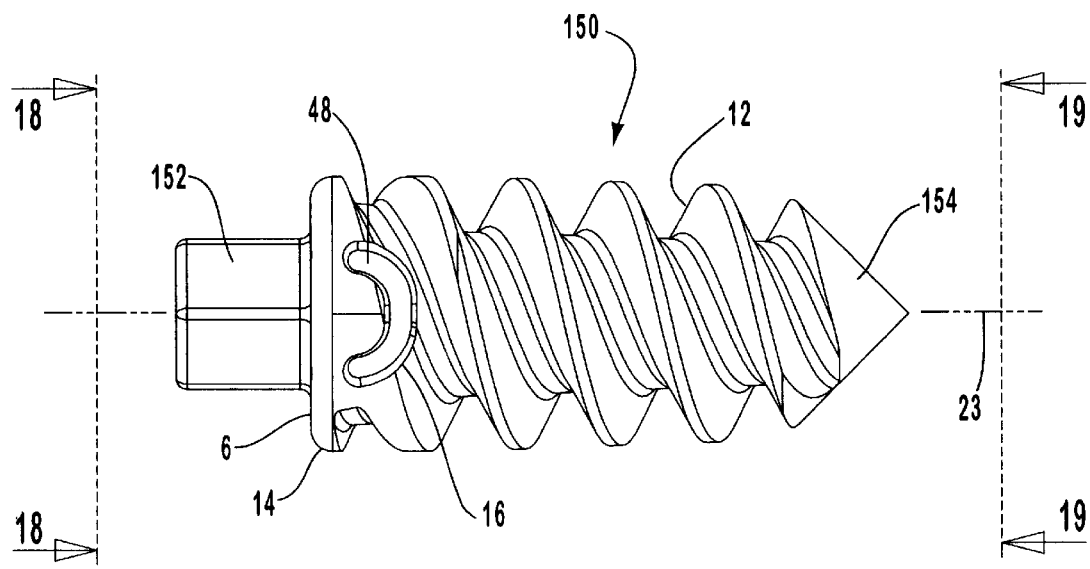
FIG. 16 is a front side view of an alternative embodiment of a suture anchor having a drive head formed thereon.
Figure 17:
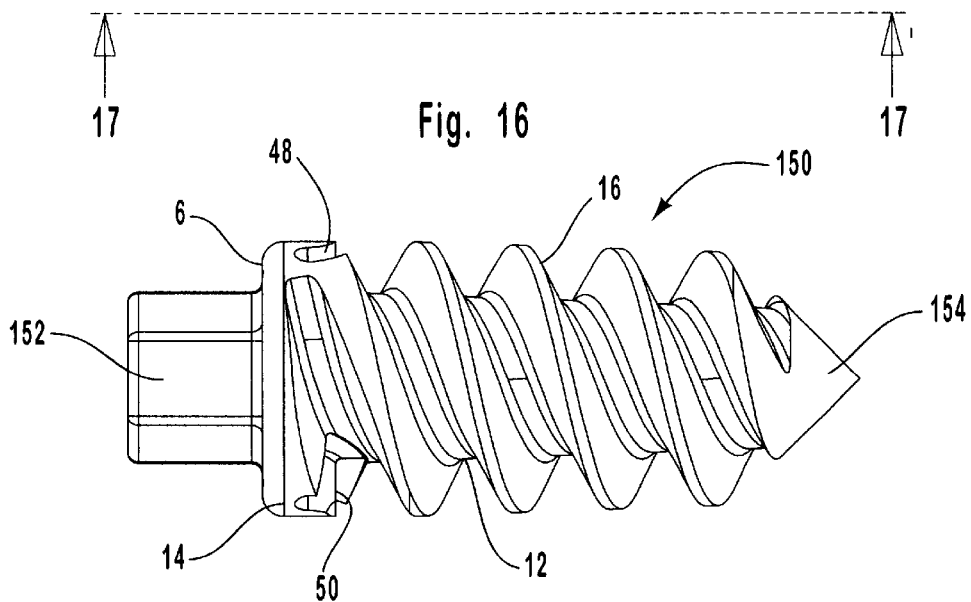
FIG. 17 is a left side view of the suture anchor shown in FIG. 16.
Figure 18:
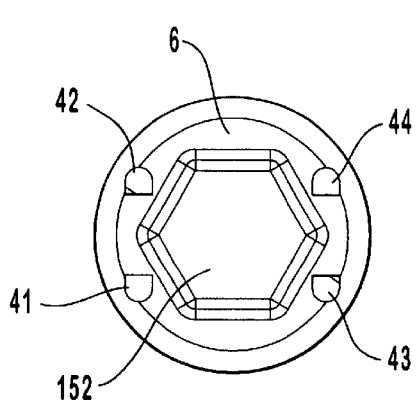
FIG. 18 is a top plan end view of the suture anchor shown in FIG. 16.

Another alternative embodiment of the engagement means is shown in FIGS. 16 and 17. As depicted therein, an alternative embodiment of a suture anchor 150 is shown with like elements between suture anchor 150 and suture anchor 10 being referred to with like reference characters. In contrast to shaft 12 of suture anchor 10 which bounds bore 58, shaft 12 of suture anchor 150 solid. As a result, shaft 12 extends to a pointed distal end 154 (also seen in FIG. 19) as opposed to a flattened distal end face. Pointed distal end 154 can also be formed on suture anchor 120 as previously discussed. To facilitate rotation of suture anchor 150, a drive head 152 outwardly project from proximal end face 6 in alignment with axis 23. Drive head 152 is smaller in diameter than flange 14 so as to provide room for suture ports 41–44 as depicted in FIG. 18.

As discussed below, drive head 152 is configured to be engaged by a complementary driver. Therefore, drive head 152 typically has a non-circular transverse cross section such as an elliptical, polygonal, irregular, or any other shape such that when the driver engages drive head 152, rotation of the driver facilitates rotation of suture anchor 150. In the embodiment depicted, drive head 152 has a hexagonal transverse cross-section. In yet other alternative embodiments, drive head can have a circular transverse cross section or any other desired shape which includes slots, groove, sockets or any other form of recess that would enable a driver to engage with the drive head.

Depicted in FIG. 20 is one embodiment of a driver 160 for engaging drive head 152 of suture anchor 150. Driver 160 includes a drive rod 162 having a head 164 formed on the end thereof. A socket 166 is formed on head 164. As discussed above, socket 166 is configured to complementary mate with drive head 152 of suture anchor 150 such that rotation of driver 160 facilitates rotation of suture anchor 150.

Depicted in FIGS. 21–30 are alternative embodiments of suture anchors showing examples of alternative features including examples of alternative suture port and/or channel configurations and placements. It is appreciated that the various features and alternatives discussed with the various suture anchors disclosed herein can be mixed and matched to form a variety of yet other suture anchor configures which are within the scope of the present invention. Like elements between the illustrated suture anchors and suture anchor 10 are identified by like reference characters.

Figure 19:
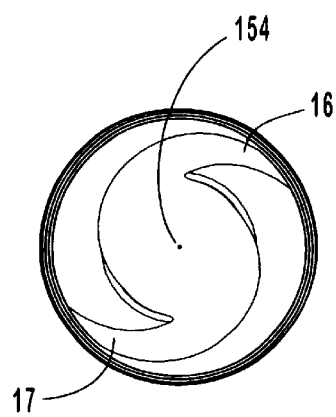
FIG. 19 is a bottom plan view of the suture anchor shown in FIG. 16.
Figure 23:
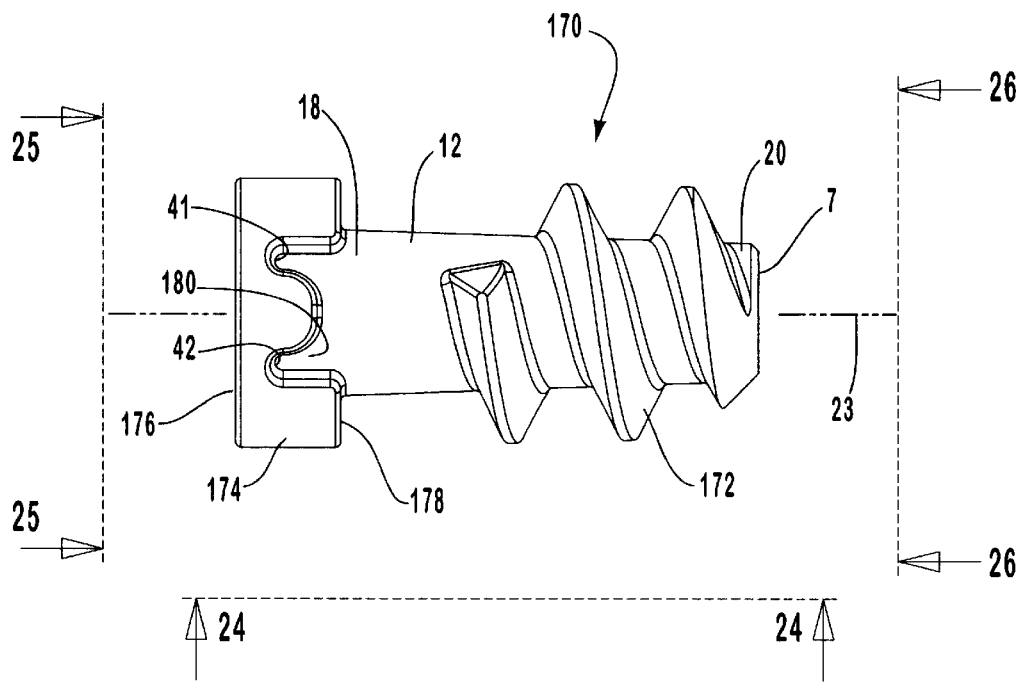
FIG. 23 is a front side view of an alternative embodiment of a suture anchor having a single thread and a flange formed thereon.
Figure 24:
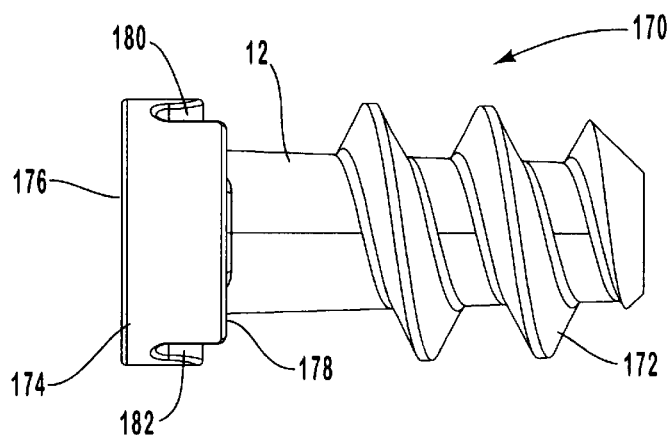
FIG. 24 is a left side view of the suture anchor shown in FIG. 23.
Figure 25:
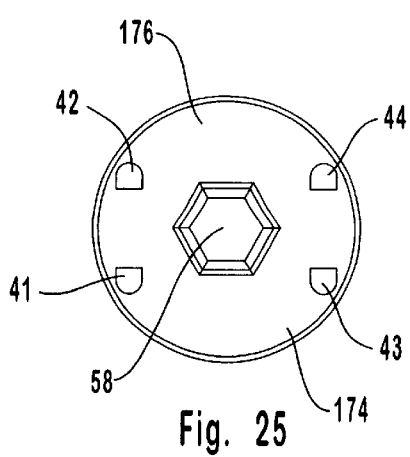
FIG. 25 is a top plan view of the suture anchor shown in FIG. 23.
Figure 26:
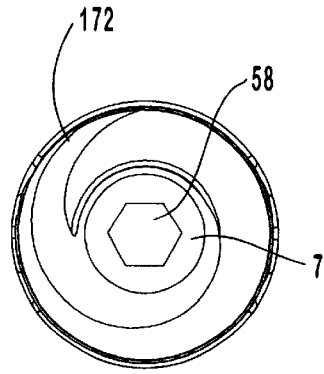
FIG. 26 is a bottom plan view of the suture anchor shown in FIG. 23.
Figure 27:
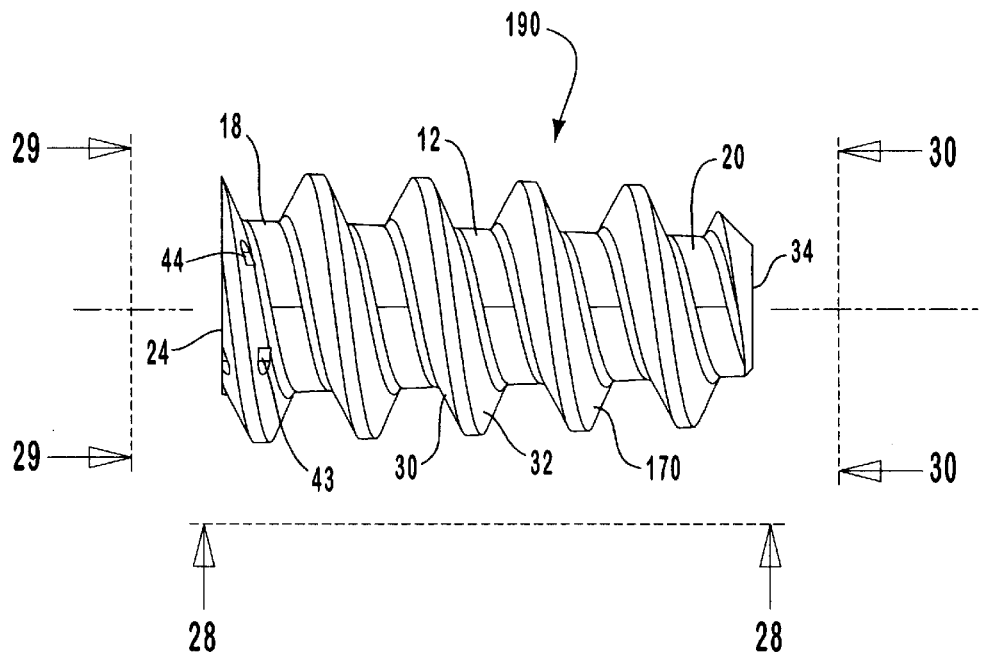
FIG. 27 is a front side view of an alternative embodiment of a suture anchor having a single thread extending along the full length thereof.
Figure 28:
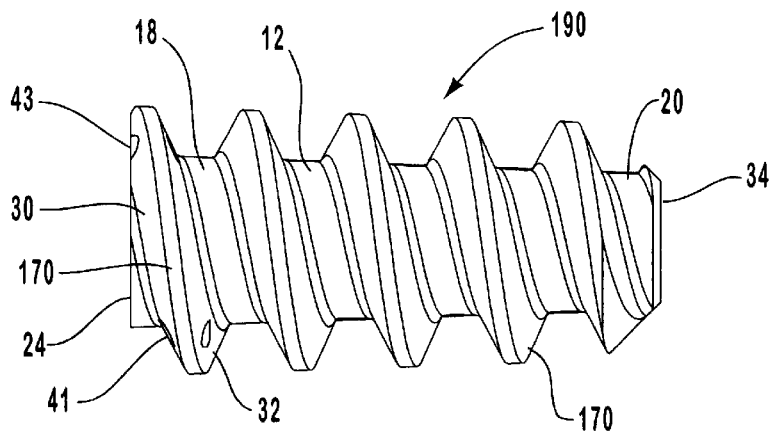
FIG. 28 is a left side view of the suture anchor shown in FIG. 27.
Figures 29, 30:
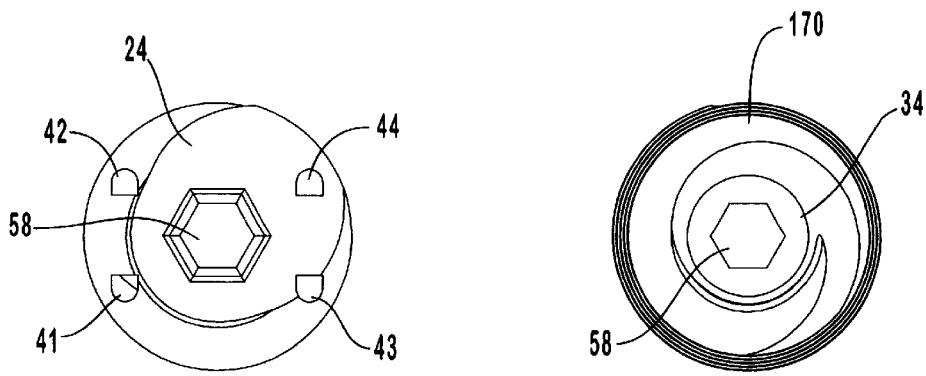
FIG. 29 is a top plan view of the suture anchor shown in FIG. 27.
FIG. 30 is a bottom plan view of the suture anchor shown in FIG. 27.

Initially, depicted in FIG. 19 is a suture anchor 100. Similar to suture anchor 10, suture anchor 100 has suture ports 41 and 42 extending into proximal end face 6. In contrast to having U-shaped channel 48, however, suture anchor 100 has a channel 102 extending from distal end 47 of suture port 41 to helical groove 28. A free end 106 of a suture line 104 is passed through suture port 41. A knot is tied at free end 106 of suture line 104 to prevent free end 106 from accidentally passing back through suture port 41.

In contrast to the use of a channel that extends to a helical groove, distal end 47 of suture port 42 merely terminates on the outside face of thread 16. A counter bore can be formed at distal end 47 of suture port 42 so that a suture knot can be at least partially received therein. In like manner, it is also appreciated that by increasing the thickness of flange 14, distal end 47 of suture port 42 can also terminate on the outside face of flange 14.

Suture anchor 100 is also distinguished from suture anchor 10 in that suture anchor 100 is limited to two suture ports, i.e., suture ports 41 and 42. In yet another alternative embodiment, a suture anchor 110 is depicted in FIG. 22 having a single suture port 112 formed thereon. It is appreciated that various alternative embodiments of suture anchors can have as many suture ports as is desired or as there is room to form.

Depicted in FIGS. 23–26 is another alternative embodiment of a suture anchor 170. Suture anchor 170 includes tubular shaft 12 extending between proximal end 18 and distal end 20. Bore 58 (FIG. 22) extends through shaft 12 to facilitation rotation of shaft 12 as previously discussed. In contrast to the use of dual intertwined helical threads 16 and 17 of suture anchor 10, suture anchor 170 includes a single helical thread 172 encircling and outwardly projecting from shaft 12. Radially outwardly projecting from proximal end 18 of shaft 12 is an enlarged annular flange 174. Flange 174 has a proximal end face 176 and an opposing distal end face 178. Helical thread 172 is spaced apart distal end face 178 of flange 174.

Suture ports 41–44 extend through flange 174 between opposing end faces 176 and 178. Although not required, to facilitate a single suture line to smoothly travel between suture ports 41 and 42 or 43 and 44, an open U-shaped channel 180 is formed on distal end face 178 of flange 174 extending between suture ports 41 and 42. Similarly, a U-shaped channel 182 is formed on distal end face 178 of flange 174 extending between suture ports 43 and 44.

Depicted in FIGS. 27–30 is yet another alternative embodiment of a suture anchor 190. Suture anchor 190 includes tubular shaft 12 extending between proximal end 18 and distal end 20. Bore 58 (FIG. 25) extends through shaft 12 to facilitation rotation of shaft 12 as previously discussed. Similar to suture anchor 170, a single helical thread 172 encircles and outwardly projects from shaft 12 of suture anchor 190. Helical thread 172 has proximal end face 30 and opposing distal end face 32. In contrast to suture anchor 170, however, suture anchor 190 does not include flange 174. Rather, helical thread 172 extends all the way to proximal end face 24 of shaft 12.

Sutures ports 41–44 extend between opposing faces 30 and 32 of helical thread 172 so as to facilitate the attachment of one or more suture lines. If desired, counter bores can be formed at the distal end of suture ports 41–44 to partially receive a suture knot. Alternatively, a recessed channel can be formed on distal end face 32 of thread 172 extending between suture ports 41–42 and/or 43–44. In another alternative embodiment, it is appreciated that in contrast to the use of single helical thread 172, dual intertwined helical threads 16 and 17 can be formed on shaft 12 of suture anchor 170, each thread extending to proximal end face 24. In this embodiment, suture ports 41 and 42 can be formed on one of threads 16 and 17 while suture ports 43 and 44 are formed on the other of threads 16 and 17.

A method of use of the various embodiments of the suture anchors will now be described with reference to FIGS. 31–35. The following description will be made with reference to suture anchor 10 unless otherwise indicated. It is appreciated, however, that the other embodiments of the suture anchor may be employed in substantially the same manner and that the following description is given only by way of example and not by limitation.

Figure 31:
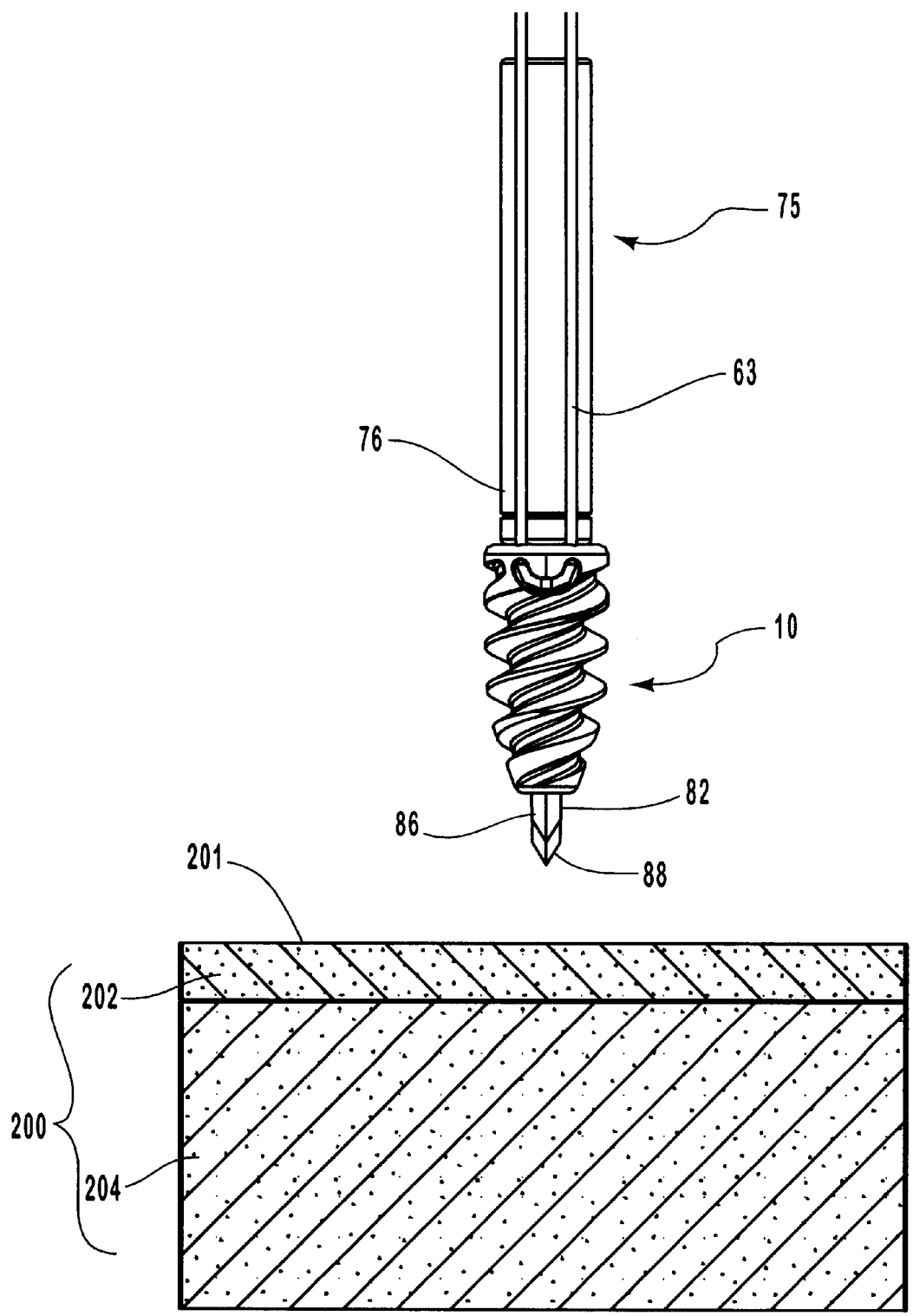
FIG. 31 is a side view of a suture anchor assembly in position for attachment to a bone.

Depicted in FIG. 31 is a bone 200 having an exterior surface 201. Bone 200 typically comprises an outer hard cortical bone layer 202 bounding a softer cancellous bone layer 204. With suture anchor 10 secured to driver 75, as previously discussed, exposed tip 86 of drive portion 82 is positioned against exterior surface 201 of bone 202. Driver 75 is then rotated causing sharpened edges 88 of drive portion 82 to burrow into bone 200.

Figure 32:
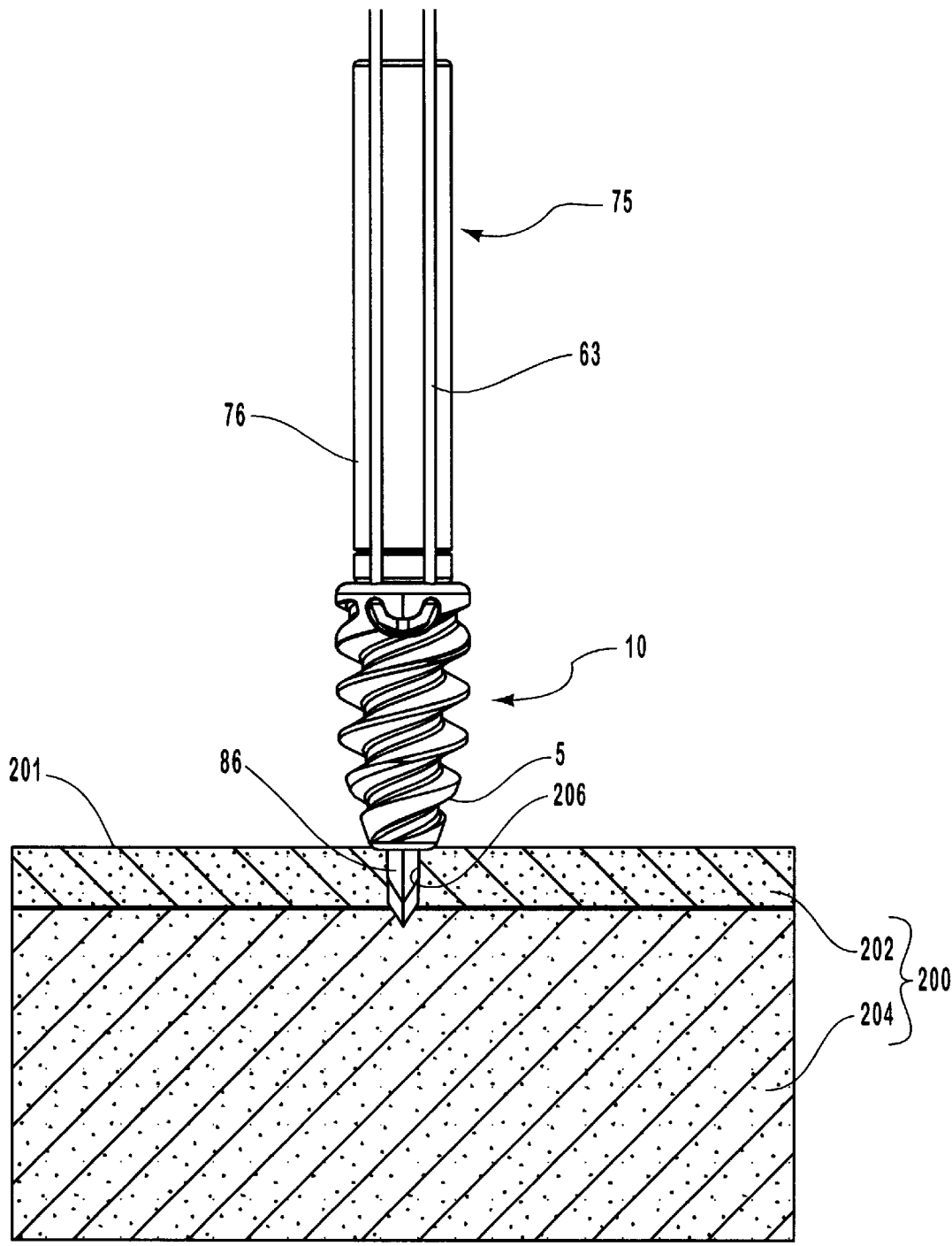
FIG. 32 is a side view of the suture anchor assembly shown in FIG. 31 with a tip of the drive rod thereof being bored into the bone.

As depicted in FIG. 32, tip 86 of drive rod 76 forms a pilot hole 206 into which distal end 5 of suture anchor 10 is initially received for facilitating threaded engagement with bone 202.

Figure 33:
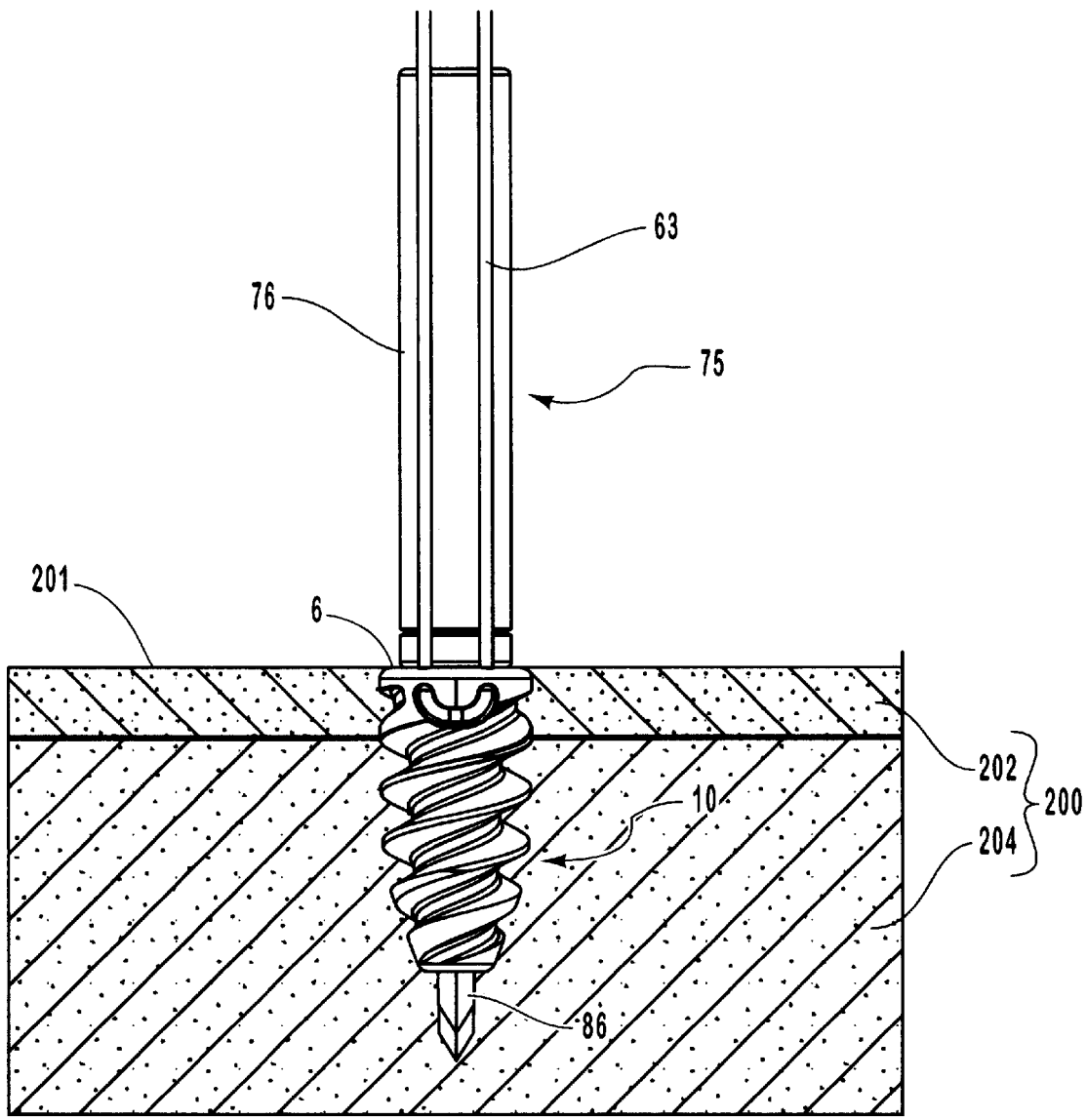
FIG. 33 is a side view of the suture anchor assembly shown in FIG. 31 with the suture anchor thereof being fully driven into the bone.
Figure 34:
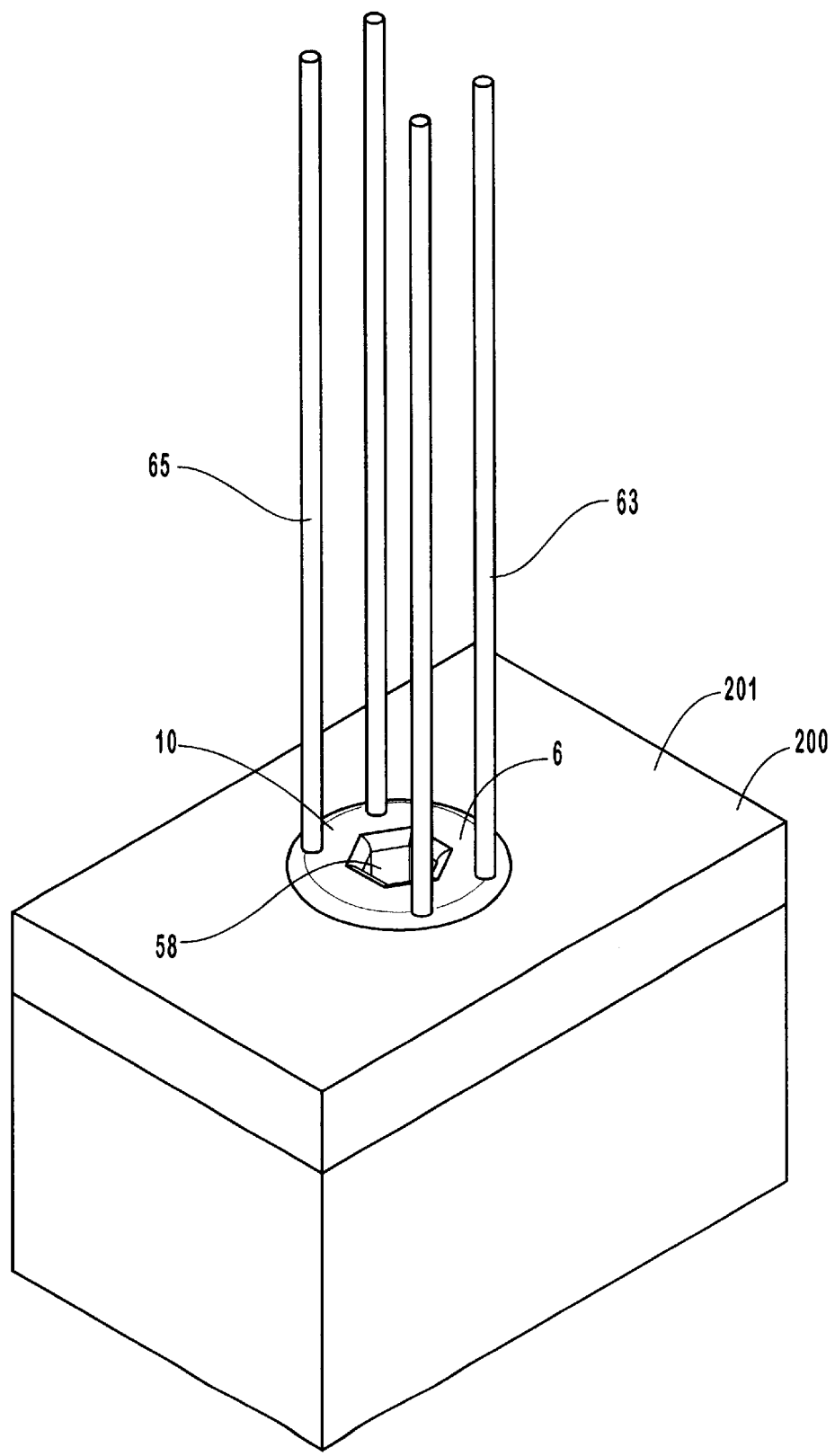
FIG. 34 is a perspective view of the suture anchor shown in FIG. 31 placed in the bone with the drive rod removed therefrom.
Figure 35:
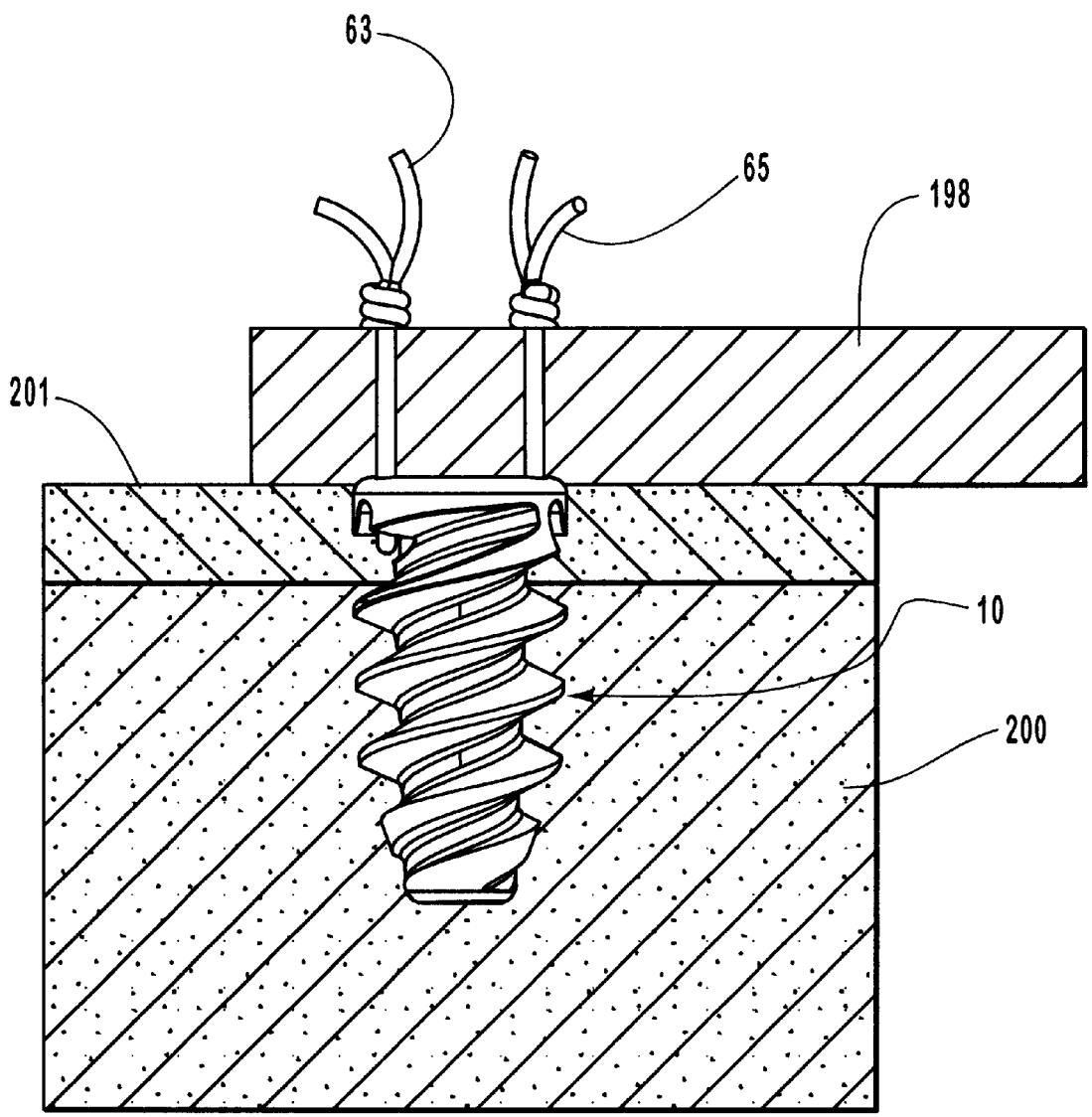
FIG. 35 is a side view of the suture anchor shown in FIG. 34 securing soft tissue to the bone.

Depicted in FIG. 33, rotation of driver 75 is continued causing suture anchor 10 to screw into bone 200 following tip 86 of drive rod 76. Suture anchor 10 is typically advanced until proximal end face 6 of suture anchor 10 is flush with exterior surface 201 of bone 200. When insertion of suture anchor 10 is completed, driver 75 is removed from suture anchor 10, as shown in FIG. 34, leaving suture lines 63 and 65 free for use by the surgeon. Finally, as shown in FIG. 35, suture lines 63 and 65 are used in a conventional manner to secure soft tissue 198, such as ligaments, tendons, muscles, and the like, to bone 200.

It is appreciated that insertion of the various suture anchors of the present invention does not require exposed tip 86 of drive rod 76. For example, suture anchor 120 depicted in FIG. 15 and suture anchor 150 depicted in FIG. 16 are inserted without the use of exposed tip 86. In these embodiment, an initial pilot hole is formed in bone 200 such as by the use of a drill or punch. The distal end of the suture anchor is then positioned within the pilot hole. The corresponding driver is then used to rotate the suture anchor such that the suture anchor is screwed into the bone. In one embodiment, it is appreciated that the pilot hole can be substantially the same size as shaft 12 such that it is only required to screw the threads into the bone. Where the bone is relatively soft, it is also appreciated that suture anchors having a pointed distal end, such as pointed distal end 154 of suture anchor 150 (FIG. 16), can be directly screwed into the bone without the formation of a pilot hole.

The various suture anchors of the present invention can be made in a variety of different ways using a variety of one or more different materials. By way of example and not by limitation, the various suture anchors can be made from medical grade bioabsorbable or non-absorbable materials. Examples of bioabsorbable materials include homopolymers and copolymers of lactide, glycolide, trimethylene carbonate, caprolactone, and p-dioxanone and blends or other combinations thereof and equivalents thereof. Examples of non-absorbable materials include metals such as stainless steel, titanium, Nitinol, cobalt, alloys thereof, and equivalents thereof and polymeric materials such as non-absorbable polyesters, polyamides, polyolefins, polyurethanes, and polyacetals and equivalents thereof.

The suture anchors may be manufactured as a single piece using standard shaping or molding techniques. Alternatively, discrete elements of the suture anchors can be manufactured separately and then connected together using conventional methods and materials. In such an embodiment, each discrete element may be made from the same or different materials.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture anchor comprising:
   an elongated shaft having an exterior sidewall extending between a proximal end and an opposing distal end;
   a helical first thread wound about and outwardly projecting from the exterior sidewall of the shaft so as to extend between the proximal end and the distal end of the shaft, the first thread having a helical proximal face and helical distal face; and
   a first suture port transversely extending through at least a portion of the first thread at the proximal end of the shaft, the first suture port being orientated such that the first suture port extends at least from toward the helical proximal face to toward the helical distal face.

2. A suture anchor as recited in claim 1, wherein the first suture port extends into the first thread from the helical proximal face, an open channel being formed on the helical distal face of the first thread so as to communicate with the first suture port.

3. A suture anchor as recited in claim 1, wherein the first suture port transversely extends entirely through the first thread.

4. A suture anchor as recited in claim 1, further comprising a second suture port transversely extending through at least a portion of the first thread at the proximal end of the shaft.

5. A suture anchor as recited in claim 4, wherein the first suture port and the second suture port extend into the first thread from the helical proximal face, an open channel being formed on the helical distal face of the thread, the channel extending between the first suture port and the second suture port.

6. A suture anchor as recited in claim 5, further comprising a helical second thread wound about the exterior sidewall of the shaft so as to extend between the proximal end and the distal end of the shaft.

7. A suture anchor as recited in claim 6, further comprising a third suture port and a fourth suture port each transversely extending through at least a portion of the second thread at the proximal end of the shaft.

8. A suture anchor as recited in claim 1, wherein the exterior sidewall of the shaft slopes radially inward toward the distal end of the shaft.

9. A suture anchor as recited in claim 1, further comprising means for mechanically engaging at least a portion of the shaft so as to enable rotational placement of the shaft.

10. A suture anchor as recited in claim 9, wherein the means for mechanically engaging comprises a bore extending through the shaft from between the proximal end and the distal end thereof.

11. A suture anchor as recited in claim 10, wherein the bore has a polygonal transverse cross section.

12. A suture anchor as recited in claim 10, wherein the bore is bounded by an interior surface that radially inwardly slopes toward the distal end.

13. A suture anchor as recited in claim 9, wherein the means for mechanically engaging comprises a closed end socket recessed within the proximal end of the shaft.

14. A suture anchor as recited in claim 9, wherein the means for mechanically engaging comprises a drive head outwardly projecting from the proximal end of the shaft.

15. A suture anchor comprising:
    a substantially cylindrical body having an exterior sidewall extending between a proximal end and an opposing distal end, the proximal end terminating at a proximal end face;
    a helical first groove recessed into and about the exterior sidewall of the body so as to extend between the proximal end and the distal end of the body;
    a bore extending through the proximal end face of the body and projecting toward the distal end of the body, the bore being disposed along a central longitudinal axis of the body; and
    a first suture port extending through the proximal end face of the body so as to communicate with the helical first groove.

16. A suture anchor as recited in claim 15, further comprising an open channel extending from the helical first groove to the first suture port.

17. A suture anchor as recited in claim 15, further comprising a second suture port extending through the proximal end face of the body so as to communicate with the helical first groove.

18. A suture anchor as recited in claim 15, wherein the helical first groove terminates distal of the proximal end face.

19. A suture anchor as recited in claim 15, wherein the bore extends entirely through the body between the proximal end and the distal end thereof.

20. A suture anchor as recited in claim 15, wherein the bore has a polygonal transverse cross section.

21. A suture anchor as recited in claim 15, wherein the bore is bounded by an interior surface that radially inwardly slopes toward the distal end.

22. A suture anchor as recited in claim 15, further comprising a helical second groove recessed into and about the exterior sidewall of the body so as to extend between the proximal end and the distal end of the body.

23. A suture anchor comprising:
    an elongated shaft having an exterior sidewall extending between a proximal end and an opposing distal end, the shaft having an interior surface bounding a bore projecting into the proximal end of the shaft toward the distal end;
    a flange radially outwardly projecting from the proximal end of the shaft;
    a helical first thread wound about and outwardly projecting from the exterior sidewall of the shaft, the first thread extending from the flange to the distal end of the shaft and bounding a helical groove; and
    a first suture port extending through the flange so as to communicate with the helical groove.

24. A suture anchor as recited in claim 23, wherein the first suture port transversely extends at least partially through the helical first thread.

25. A suture anchor as recited in claim 24, wherein the first thread has a first side and an opposing second side, the first suture port extending into the first thread from the first side, an open channel being formed on the second side of the first thread so as to communicate with the first suture port.

26. A suture anchor as recited in claim 23, further comprising a second suture port extending through the flange.

27. A suture anchor as recited in claim 23, further comprising an open channel extending between the first suture port and the second suture port.

28. A suture anchor as recited in claim 26, further comprising a third suture port and a fourth suture port each extending through the flange.

29. A suture anchor as recited in claim 23, wherein the bore has a polygonal transverse cross section.

30. A suture anchor as recited in claim 23, wherein the interior surface of the bore radially inwardly slopes toward the distal end.

31. A suture anchor as recited in claim 23, wherein the bore extends through the shaft between the proximal end the distal end thereof.

32. A suture anchor comprising:
- an elongated shaft having an exterior sidewall extending between a proximal end and an opposing distal end, the shaft having an interior surface bounding a bore extending through the shaft from the proximal end to the distal end;
- a flange radially outwardly projecting from the proximal end of the shaft, the flange have a proximal end face and an opposing distal end face;
- a helical first thread wound about and outwardly projecting from the exterior sidewall of the shaft, the first thread being distally spaced apart from the flange; and
- a first suture port extending between the proximal end face and the distal end face of the flange.

33. A suture anchor as recited in claim 32, further comprising a second suture port extending between the proximal end face and the distal end face of the flange.

34. A suture anchor as recited in claim 32, further comprising a third suture port and a fourth suture port each extending between the proximal end face and the distal end face of the flange.

35. A suture anchor as recited in claim 32, wherein the bore has a non-circular transverse cross section.

36. A suture anchor as recited in claim 32, wherein the interior surface of the bore radially inwardly slopes toward the distal end.

37. A suture anchor assembly comprising:
- a suture anchor comprising:
  - a tubular shaft having an exterior sidewall extending between a proximal end and an opposing distal end, the shaft having an interior surface bounding a bore extending between the proximal end and the distal end; and
  - a helical first thread wound about and outwardly projecting from the exterior sidewall of the shaft so as to extend between the proximal end and the distal end of the shaft;
- a first suture port formed on the suture anchor; and
- an elongated drive rod having a proximal end and an opposing distal end, the distal end including a drive portion terminating at a tip, the tip having a plurality of sharpened edges adapted to burrow into bone upon rotation of the drive rod, the drive portion being configured to be selectively received within the bore of the suture anchor such that the tip of the drive portion extends past the distal end of the shaft of the suture anchor.

38. A suture anchor assembly as recited in claim 37, wherein at least a portion of the drive portion of the drive rod and at least a portion of the interior surface of the shaft are configured to complementarily mate so that rotation of the drive rod facilitates rotation of the shaft.

39. A suture anchor assembly as recited in claim 37, wherein the entire length of the bore extending through the shaft of the suture anchor has a configuration complementarily to the drive portion of the drive rod received within the bore.

40. A suture anchor assembly as recited in claim 37, wherein the bore and the drive portion received within the bore each have a polygonal transverse cross section.

41. A suture anchor assembly as recited in claim 37, wherein a first suture port transversely extends through at least a portion of the first thread at the proximal end of the shaft.

42. A suture anchor assembly as recited in claim 41, further comprising a second suture port transversely extending through at least a portion of the first thread at the proximal end of the shaft.

43. A suture anchor assembly as recited in claim 42, further comprising a single suture extending through both the first suture port and the second suture port, the shaft separating the suture from the bore.

44. A suture anchor assembly as recited in claim 37, wherein the suture anchor further comprises a flange outwardly projecting from the proximal end of the shaft, the first suture port extending through the flange.

45. A method for using the suture anchor assembly according to claim 37, the method comprising:
- forming a pilot hole at a point of attachment on a bone;
- placing the tip of the drive rod in the pilot hole;
- rotating the drive rod such that the tip of the drive rod burrows into the bone and the suture anchor screws into the bone following the tip of the drive rod: and
- removing the drive rod from the suture anchor screwed into the bone.

46. A method for using the suture anchor assembly according to claim 37, the method comprising:
- placing the tip of the drive rod at a point of attachment on a bone;
- rotating the drive rod such that the tip of the drive rod burrows into the bone forming a pilot hole at the point of attachment;
- continuing to rotate the drive rod such that the suture anchor screws into the bone through the pilot hole formed by the drive rod; and
- removing the drive rod from the suture anchor screwed into the bone.

47. A suture anchor comprising:
- an elongated shaft having an exterior sidewall extending between a proximal end and an opposing distal end;
- a helical first thread wound about and outwardly projecting from the exterior sidewall of the shaft so as to extend between the proximal end and the distal end of the shaft;
- a first suture port transversely extending through at least a portion of the first thread at the proximal end of the shaft; and
- a second suture port transversely extending through at least a portion of the first thread at the proximal end of the shaft.

48. A suture anchor comprising:
- an elongated body having a central longitudinal axis and an exterior sidewall each extending between a proximal end and an opposing distal end, a helical first groove being recessed into and about the exterior sidewall of the body;
- a first suture port extending through a portion of the body, the first suture port being spaced apart from the central longitudinal axis of the body so as to not intersect with the central longitudinal axis of the body; and
- a suture disposed within the first suture port.

49. A suture anchor as recited in claim 48, wherein the body has a proximal end face, the first suture port extending at least partially through the proximal end face.

50. A suture anchor as recited in claim 49, further comprising a bore extending through the proximal end face of the body and projecting toward the distal end of the body, the bore being disposed along the central longitudinal axis of the body.

51. A suture anchor as recited in claim 48, wherein the body comprises a helical thread at least partially bounded by the helical first groove, the first suture port extending at least partially through the helical thread.

52. A suture anchor as recited in claim 48, further comprising a second suture port extending through a portion of the body.

53. A suture anchor as recited in claim 48, wherein the first suture port has a central longitudinal axis that is substantially parallel with and radially offset from the central longitudinal axis of the elongated body.

* * * * *

UNITED STATES PATENT AND TRADEMARK OFFICE
CERTIFICATE OF CORRECTION

PATENT NO. : 6,685,728 B2
DATED : February 3, 2004
INVENTOR(S) : Sinnotte et al.

It is certified that error appears in the above-identified patent and that said Letters Patent is hereby corrected as shown below:

Column 6,
Line 12, change "feed" to -- fed --

Column 7,
Line 1, before "driver" replace "an" with -- a --
Lines 21-22, change "complementary" to -- complementarily --
Line 30, before "shaft" insert -- of --
Line 57, before "mates" change "complementary" to -- complementarily --

Column 9,
Line 21, before "rotation" change "facilitation" to -- facilitate --

Column 10,
Line 35, change "embodiment," to -- embodiments," --

Column 13,
Line 7, after "proximal end" insert -- and --
Line 16, after "flange" change "have" to -- having --
Lines 62-63, change "complementarily" to -- complementary --

Signed and Sealed this

Eighth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,685,728 B2
DATED : February 3, 2004
INVENTOR(S) : Sinnott et al.

It is certified that error appears in the above-identified patent and that said Letters Patent is hereby corrected as shown below:

Column 6,
Line 12, change "feed" to -- fed --.

Column 7,
Line 21, before "driver" replace "an" with -- a --
Lines 21-22, change "complementary" to -- complementarily --
Line 30, before "shaft" insert -- of --
Line 57, before "mates" change "complementary" to -- complementarily --

Column 8,
Line 1, before "distance" insert -- a --
Line 2, change "bound" to -- bounds --
Line 19, after "suture anchor 150" insert -- is --
Line 24, after "outwardly" change "project" to -- projects --
Line 45, after "configured to" change "complementary" to -- complementarily --

Column 9,
Line 21, before "rotation" change "facilitation" to -- facilitate --

Column 10,
Line 35, change "embodiment," to -- embodiments, --

Column 13,
Line 7, after "proximal end" insert -- and --
Line 16, after "flange" change "have" to -- having --
Lines 62-63, change "complementarily" to -- complementary --

Signed and Sealed this

Fifteenth Day of June, 2004

JON W. DUDAS
*Acting Director of the United States Patent and Trademark Office*